(12) United States Patent
Barnicki et al.

(10) Patent No.: US 6,395,913 B1
(45) Date of Patent: May 28, 2002

(54) RECOVERY AND PURIFICATION OF 3,4-EPOXY-1-BUTENE

(75) Inventors: Scott Donald Barnicki, Kingsport, TN (US); Jerome Leonard Stavinoha, Jr., Longview, TX (US); Robert Sterling Kline, Talbott; Jackie Lee Hamilton, Jonesborough, both of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/910,359

(22) Filed: Jul. 20, 2001

(51) Int. Cl.[7] .................... C07D 301/32; C07D 301/10
(52) U.S. Cl. ................... 549/538; 549/534; 549/536
(58) Field of Search ..................... 549/538, 534, 549/536

(56) References Cited

U.S. PATENT DOCUMENTS

| | | |
|---|---|---|
| 2,773,844 A | 12/1956 | Carlson et al. |
| 3,418,338 A | 12/1968 | Gilman et al. |
| 3,644,432 A | 2/1972 | Hoch et al. |
| 3,745,092 A | 7/1973 | Vanderwater |
| 3,948,621 A | 4/1976 | Cocuzza et al. |
| 3,962,136 A | 6/1976 | Nielsen et al. |
| 3,964,980 A | 6/1976 | Ozero |
| 4,221,727 A | 9/1980 | Tsang et al. |
| 4,233,221 A | 11/1980 | Raines et al. |
| 4,356,312 A | 10/1982 | Nielsen et al. |
| 4,437,938 A | 3/1984 | Bhise et al. |
| 4,437,939 A | 3/1984 | Bhise et al. |
| 4,897,498 A | 1/1990 | Monnier et al. |
| 4,950,773 A | 8/1990 | Monnier et al. |
| 5,081,096 A | 1/1992 | Monnier et al. |
| 5,117,012 A | 5/1992 | Stavinoha, Jr. et al. |
| 5,312,931 A | 5/1994 | Stavinoha, Jr. |
| 5,529,667 A | 6/1996 | Coffey |
| 5,559,255 A | 9/1996 | Kawabe et al. |
| 5,618,954 A | 4/1997 | Boeck et al. |
| 6,018,061 A | 1/2000 | Barnicki et al. |

OTHER PUBLICATIONS

Dever et al., Ethylene Oxide, Kirk–Othmer Encyclopedia of Chemical Technology, 4th Ed., vol. 9, 1994, pp. 924–939.

Kister, H. Z. Distillation Design, McGraw–Hill, N.Y. (1992), Chapter 6.

Kister, H. Z. Distillation Design, McGraw–Hill, N.Y. (1992), Chapter 8.

*Primary Examiner*—Ba K. Trinh
(74) *Attorney, Agent, or Firm*—Michael J. Blake; Bernard J. Graves, Jr.

(57) ABSTRACT

Disclosed is a method of recovering and purifying 3,4-epoxy-1-butene (epoxybutene) from a reaction product gas, obtained by the vapor phase catalytic partial oxidation of 1,3-butadiene with oxygen over a silver catalyst. The recovery and purification comprises absorption of the epoxybutene into a water-miscible solvent followed by separation of the absorbed epoxybutene from the absorbent by extraction into a water-immiscible solvent. A method of recovering and purifying epoxybutene from the extraction solvent and other reaction by-products by a novel combination of distillation and decantation steps also is disclosed.

26 Claims, 2 Drawing Sheets

RECOVERY AND PURIFICATION OF 3,4-EPOXY-1-BUTENE

FIELD OF THE INVENTION

The present invention relates to a method of recovering and purifying 3,4-epoxy-1-butene (epoxybutene) from a reaction product gas, obtained by the vapor phase catalytic partial oxidation of 1,3-butadiene with oxygen over a silver catalyst. More specifically, the present invention relates to a method of recovering epoxybutene from an epoxybutene-laden reaction product gas by absorption into a water-miscible solvent, followed by separation of the absorbed epoxybutene from the absorbent by extraction into a water-immiscible solvent. This invention also relates to a method of recovering and purifying epoxybutene from the extraction solvent and other reaction by-products by a novel combination of distillation and decantation steps.

BACKGROUND OF THE INVENTION

Ethylene oxide (EO) and epoxybutene are produced by processes which involve the catalytic, partial oxidations of the corresponding olefin, i.e., ethylene and butadiene, with oxygen in the presence of a silver catalyst. See, for example, U.S. Pat. Nos. 2,773,844 and 3,962,136, and 4,356,312 for ethylene oxide and U.S. Pat. Nos. 4,897,498, 4,950,773, and 5,081,096 for 1,2-epoxy-3-butene. Considerable effort has been devoted to the development of efficient methods of recovering these epoxides, particularly EO, from the reaction product gas and subsequent purification of the epoxide.

According to U.S. Pat. Nos. 3,745,092 and 3,964,980, and Dever et al, Ethylene Oxide, in Kirk-Othmer Encyclopedia of Chemical Technology, 4th Ed., 1994, pp. 929–930), EO is recovered and purified according to the following steps. A reaction product gas typically containing 0.5 to 5% EO, obtained by the vapor phase catalytic oxidation of ethylene with oxygen in the presence of a silver catalyst, is introduced to an EO absorption tower where it is contacted counter-currently with an absorbent comprised mostly of water, within which absorbs the EO. The absorber is typically maintained at a temperature of 5 to 40° C. and 10 to 30 bar absolute (bara).

The EO-laden absorbent is then sent to a distillation (stripping) column wherein vaporous EO is recovered from the top of the tower at a temperature of 85 to 140° C. by steam stripping at reduced pressure. The water remaining after the distillation of EO is recycled to the absorption tower for reuse. EO reacts readily with water under absorption and distillation conditions to form ethylene glycol, which can react further to form diethylene glycol, triethylene glycol, and higher oligomers. Although ethylene glycol is a valuable and marketable chemical, diethylene glycol and higher oligomers have much less commercial demand and are thus generally undesirable by-products. Formation of ethylene glycol oligomers can be controlled to some extent by limiting ethylene glycol concentration in the recycled water to the absorber. Typical levels are less than 10 weight percent ethylene glycol in the recycled absorber water.

The crude EO vapor recovered in the stripper overhead comprises EO as the main component, as well as impurities such as water, argon, nitrogen, carbon dioxide, methane, ethane and ethylene, formaldehyde, and acetaldehyde. The light or low-boiling components, e.g., nitrogen, carbon dioxide, argon, methane, ethane, and ethylene are removed overhead in a second stripping column. The partially purified EO is removed from the upper section or top of the second stripping column and is transferred to the mid-section of a refining column for final purification. U.S. Pat. Nos. 5,529,667 and 3,418,338 disclose the use of extractive distillation with water as a solvent in either the second stripping column or the refining column to reduce the level of aldehyde impurities in the final purified EO product.

By employing the above process steps EO purities of greater than 99.5 mole percent are possible. Although these water-based processing steps function effectively for EO recovery and purification, they cannot be employed equally efficaciously for the recovery and purification of epoxybutene. First, whereas EO is completely and infinitely miscible with water, epoxybutene is only sparingly miscible with water. At 25° C. the solubility of epoxybutene in water is only about 5 to 6 weight percent. As a result, water is a very poor absorbent for epoxybutene. High water to epoxybutene ratios, i.e., upward of 50/1 to 150/1, are required to ensure complete absorption of epoxybutene from the butadiene oxidation effluent. The use of such ratios is prohibited by the cost of the equipment and energy required.

Secondly, EO is a relatively low-boiling component compared to water, i.e., normal boiling point of 10.4° C. versus 100° C. respectively, and does not form an azeotrope with water. Thus, EO can be distilled readily from water by simple fractional distillation techniques as described above for the conventional EO recovery scheme. However, epoxybutene is much more hydrophobic than EO and forms a minimum-boiling azeotrope with water. High purity epoxybutene cannot be obtained by the simple fractional distillation techniques employed for EO recovery.

Other methods have been proposed for recovery of EO from reaction product gases. These methods are likewise not effective or are uneconomical for EpB recovery and purification. For example, U.S. Pat. No. 3,948,621 discloses a method of separating EO and carbon dioxide simultaneously from a mixed gas obtained from catalytic oxidation of ethylene by oxygen using methanol as an absorbent. As with water, epoxybutene forms a minimum-boiling azeotrope with methanol and, thus, epoxybutene and methanol cannot be separated readily by simple fractional distillation.

U.S. Pat. Nos. 4,437,938 and 4,437,939 disclose methods using supercritical or near supercritical carbon dioxide and water at the same time as absorbents. EO is first absorbed into water as in conventional recovery methods. The EO-rich aqueous absorbent is contacted with (near) supercritical carbon dioxide, and EO is extracted to the carbon dioxide solvent. The carbon dioxide is separated from EO by distillation under reduced pressure. The carbon dioxide is recompressed before recycling as the extraction solvent. This method, however, has many drawbacks. First, the required amount of (near) supercritical carbon dioxide is approximately 35 times the amount of EO to be absorbed therein, which requires large equipment. The extraction is carried out at high pressures i.e., 86 bara, while the distillation step is carried out at lower pressure, i.e., about 0.1 to 2 bara. The wide pressure differential results in high compression costs and, thus, does not provide an economical solution.

U.S. Pat. Nos. 4,221,727 and 4,233,221 discloses a method using ethylene carbonate as an absorbent for EO. Ethylene carbonate has many advantages as an absorbent. The absorption affinity of ethylene carbonate for EO is higher than that of water. The vapor pressure of ethylene carbonate is quite low, i.e., normal boiling point of 239° C., so losses into the recycle gas are minimal. Moreover, ethylene carbonate is stable and does not directly react with EO. The process disclosed in U.S. Pat. No. 4,233,221, however, has the following drawbacks for EO and EpB recovery. The most preferred temperature range for operation of conventional water absorption is 5 to 40° C. The melting point of ethylene carbonate is 39° C., so ethylene carbonate would be a solid over almost all of the preferred temperature range. In order to avoid solidification, it is necessary to operate the absorber and other processing equipment substantially above, i.e., at least 10 to 20° C., above the melting point of ethylene carbonate. This is much higher temperature than an operation using water. The absorbing power of the ethylene carbonate correspondingly decreases so that the amount of circulating absorbent must be increased, reducing the economic utility of the process.

U.S. Pat. No. 5,559,255 describes the use of propylene carbonate as an absorbent for EO. The EO-laden propylene carbonate is stripped with an inert gas to recover EO and the water by-product from the epoxidation reactor as a vapor. Purified EO is produced from the mixed water-EO vapors as in conventional methods described in U.S. Pat. Nos. 3,745,092 and 3,964,980. Unlike ethylene carbonate, propylene carbonate is a liquid at room temperature and thus offers a more robust process than ethylene carbonate absorption. However, the process described In U.S. Pat. No. 5,559,255 also has drawbacks for epoxybutene recovery and purification. Epoxybutene is a much less volatile component than ethylene oxide and cannot be removed effectively from propylene carbonate by inert gas stripping as described in the '255. Moreover, this EO process does not presage or address the problems associated with epoxybutene recovery and separation from the epoxybutene-water azeotrope, butadiene, or other impurities absorbed with epoxybutene from the epoxidation reactor product gas.

U.S. Pat. No. 3,644,432 discloses the use of liquid ethane as an absorbent for EO. The reactor product gas is cooled, compressed, and then passed through a molecular sieve drier bed to remove the by-product water of reaction. The dried reactor product gas is contacted in a counter-current absorption tower with liquid ethane at a preferred temperature range of −31.5 to −17.6° C. at a pressure of about 1.8 MPa. EO is much more soluble in liquid ethane than in water, so the solvent to feed gas ratio of the absorber can be reduced considerably from the water absorbent case, with concomitant cost reductions. However, maintenance of such cryogenic temperatures requires expensive refrigeration equipment that much more than offsets any savings due to lower solvent to feed gas ratios. Thus, there are no acceptable absorption/separation methods originally developed for EO that can be adapted readily and economically to epoxybutene absorption/separation.

The patent literature is not as extensive for epoxybutene production, but several patents address the issue of epoxybutene recovery/separation. U.S. Pat. Nos. 5,117,012 and 5,312,931 disclose the use of liquid butadiene and butadiene/butane mixtures as an absorbent for epoxybutene. The reactor product gas is cooled, compressed, and contacted in a counter-current absorption tower with liquid butadiene/n-butane at a preferred temperature range of 0 to 30° C. at a pressure of about 5 to 15 bar. Water and water-soluble impurities are removed by decantation of the epoxy-butene-rich absorbent stream. Any remaining water, butadiene/n-butane absorbent, and low-boiling impurities are removed by distillation to give a purified epoxybutene product. However, n-butane and 1,3-butadiene have relatively high volatilities, with normal boiling points of −0.5° C. and −4.5° C., respectively. In order to ensure that substantially all of the solvent n-butane/butadiene largely remains a liquid within the absorption zone at operating temperatures that can be achieved with an inexpensive cooling medium such as water, i.e., above at least about 30° C., the absorption zone must be operated at a pressure of at least about 4.2 bars. Operation at lower pressures, and concomitantly lower temperatures is quite costly if the required low temperature cooling is supplied by ordinary means to those skilled in the art such as chilled brine or glycol refrigeration units. Thus, to meet the aforementioned temperature and pressure requirements for absorption with n-butane, the reactor effluent must first be compressed to a suitable pressure, i.e., greater than about 4.2 bars, prior to its introduction into the absorption zone. The higher pressures and resulting polytropic temperature rise within the compression zone in the presence of high concentrations of epoxybutene can cause formation of polymeric materials that deposit on the walls of the compressor and associated piping. The build-up of such polymeric material reduces the operating efficiency of the compressor and can lead to permanent equipment damage and frequent process shut-downs for maintenance, with subsequent loss of production and revenues. Moreover, the large inventory in the absorption/distillation of highly volatile and explosive butadiene and butane is dangerous and leads to higher than average safety-related costs.

U.S. Pat. No. 6,018,061 addresses the problems inherent with the compression of high concentrations of epoxybutene, as exemplified in U.S. Pat. Nos. 5,117,012 and 5,312,931, by providing a compression or absorption refrigeration cycle for cooling the epoxybutene absorption zone prior to compression with the reaction diluent, i.e., C3 to C5 hydrocarbons, preferably butane/butadiene, as the refrigerant. In this fashion, the epoxybutene absorption zone can be operated at pressures less than about 4 bara and a temperature of less than about 40° C. without need for pre-compression or external refrigeration. However, with pressures in the absorption zone higher than the 4 bara specified in the '061 patent, the auto-cooling effect provided by the refrigeration cycle is greatly diminished. The temperature of the absorber becomes hotter and the absorptive power of the solvent, i.e., butane/butadiene, is greatly reduced. Thus, for example, at a pressure of 5.5 bara (80 pounds per square inch—psia), the auto-refrigeration effect provides only a temperature of about 60° C. Moreover, at pressures above 4 bara, the potential for unwanted condensation of n-butane/butadiene in equipment in the recycle loop increases dramatically. Excessive condensation can cause the recycle gas composition to become flammable, an unsafe and unacceptable operating condition. Finally, as with the processes of the '012 and '931 patents, the inventory of highly volatile and explosive butadiene and butane is large.

U. S. Pat. No. 5,618,954 discloses the recovery of epoxybutene from a butadiene epoxidation reactor effluent gas by countercurrent contact in an absorption zone with water. Epoxybutene is recovered from the water by stripping with an inert gas, similar to the conventional EO recovery process described above. As explained above, water by itself is a poor absorbent for epoxybutene and its use results in uneconomical process due to the required high water to epoxybutene ratio. Moreover, the reactor effluent from the process described in the '954 patent has been found to contain small quantities of acidic partial oxidation products, i.e., formic acid and crotonic acid. These acidic species are readily absorbed in water and rapidly catalyze the hydrolysis of epoxybutene to 3-butene-1,2-diol and other higher ether alcohols. Losses of greater than 60 percent of the absorbed epoxybutene are common. Finally, the process as described in the '954 patent is incomplete and cannot provide purified EpB. No mention is made of the binary epoxybutene-water minimum-boiling azeotrope or of methods to obtain purified epoxybutene from this azeotrope with water. Thus, the recovery efficiency of epoxybutene from such a process is expected to be low.

In view of the recovery processes described above, it is apparent that no method disclosed in the prior art is completely satisfactory for the recovery and purification of epoxybutene. Accordingly, there is a need for a process to efficiently and economically recover and purify epoxybutene from the product gas of a vapor phase epoxidation reactor.

SUMMARY OF THE INVENTION

It has been discovered that EpB can be recovered from a substantially vaporous epoxidation effluent comprising epoxybutene, oxygen, unreacted butadiene, and inert reaction diluent, e.g., methane, ethane, nitrogen, and the like, by intimately contacting the vaporous effluent with an effective amount of an water-miscible, liquid absorbent or solvent in an absorption zone, such as an absorber, to absorb essentially all of the epoxybutene present in the vaporous reactor effluent into the water-miscible absorbent. The epoxybutene-absorbent solution then is intimately contacted with an effective amount of a water-immiscible extractant in an extraction zone, such as an extractor, to extract the epoxybutene present in the water-miscible absorbent into the water-immiscible extractant. The present invention therefore provides a process for the recovery of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises the steps of:

I. feeding the effluent to an absorption vessel wherein the effluent is intimately contacted with a water-miscible, liquid absorbent to obtain:
   (i) a gaseous effluent comprising butadiene, oxygen and an inert diluent from the upper section of the absorption vessel; and
   (ii) a liquid effluent comprising epoxybutene, the absorbent and water from the lower section of the absorption vessel; and
II. feeding the liquid effluent of step (ii) above to an extraction zone wherein the effluent is intimately contacted with an inert, water-immiscible, liquid extractant to obtain:
   (iii) a first liquid effluent comprising the water-immiscible, liquid extractant and epoxybutene; and
   (iv) a second liquid effluent comprising the absorbent and water from which epoxybutene has been depleted;
   wherein
      the water-miscible, liquid absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof and the absorbent compound(s) contain 3 to about 8 carbon atoms; the water-immiscible, liquid extractant is a liquid organic compound containing 4 to about 25 carbon atoms selected from hydrocarbons, halocarbons, esters, ethers, ketones, carbonates or a mixture of any 2 or more thereof; epoxybutene is 3,4-epoxy-1-butene; and butadiene is 1,3-butadiene.

We have discovered that epoxybutene is particularly prone to reaction with water and glycols during storage, heating, mixing, and during distillative recovery of epoxybutene from water miscible solvent solutions. Thus, the present invention provides a process for the recovery of epoxybutene from the water-miscible absorbent mixtures by means other than heating and distillation. The epoxybutene-rich liquid absorber effluent is intimately contacted with an effective amount of a water-immiscible extractant in an extraction zone, such as an extractor, to extract essentially all of the epoxybutene present in the water-miscible absorber effluent. In this manner epoxybutene can be separated effectively from absorbent mixtures, without heating or the use of distillation, while minimizing its reaction with water and glycol.

Another aspect of the present invention is the separation of epoxybutene from high-boiling extractants and co-extracted species by a two-column distillation sequence with intermediate liquid-liquid phase decantation. This second embodiment of the invention provides a process for the recovery and purification of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises the steps of:

I. feeding the effluent to an absorption vessel wherein the effluent is intimately contacted with a water-miscible, liquid absorbent to obtain:
   (i) a gaseous effluent comprising butadiene, oxygen and an inert diluent from the upper section of the absorption vessel; and
   (ii) a liquid effluent comprising epoxybutene, the absorbent and water from the lower section of the absorption vessel; and
II. feeding the liquid effluent of step (ii) above to an extraction zone wherein the effluent is intimately contacted with an inert, water-immiscible, liquid extractant to obtain:
   (iii) a first liquid effluent comprising the water-immiscible, liquid extractant and epoxybutene; and
   (iv) a second liquid effluent comprising the absorbent and water from which epoxybutene has been depleted;
III. feeding liquid effluent (iii) of step II. to the middle section of a first distillation column to obtain (1) a distillate effluent comprising epoxybutene and water from the upper section of the distillation vessel and (2) a liquid effluent comprising the extractant from the lower section of the distillation vessel;
IV. allowing distillate (1) from step III. to form 2 phases comprising an epoxybutene-rich phase and a water-rich phase; and
V. feeding the epoxybutene-rich phase from step III to the upper section of an epoxybutene purification distillation column to obtain (1) a distillate effluent comprising epoxybutene and water from the upper section of the distillation vessel; and (2) an effluent comprising (a) liquid epoxybutene from the lower section of the distillation column or (b) liquid or gaseous epoxybutene from the side of the distillation column; wherein
   the water-miscible, liquid absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof and the absorbent compound(s) contain 3 to about 8 carbon atoms; the water-immiscible, liquid extractant is a liquid organic compound containing 4 to about 25 carbon atoms selected from hydrocarbons, halocarbons, esters, ethers, ketones, carbonates or a mixture of any 2 or more thereof; epoxybutene is 3,4-epoxy-1-butene; and butadiene is 1,3-butadiene.

In the first column epoxybutene is separated from the extractant and low boiler(s) present, e.g., butadiene, as a distillate mixture comprising epoxybutene and water. The epoxybutene-free solvent is recycled to the extractor for reuse. The distillate product of the first column is allowed to separate into two liquid phases in a decanter. The water-wet epoxybutene phase from the decanter is dehydrated in the epoxybutene recovery column. Epoxybutene is taken as a bottoms product, or sidedraw from near the bottom of the epoxybutene recovery column, with a distillate mixture comprising epoxybutene and water recycled to the decanter. The aqueous phase of the decanter may be recycled to the extractor for further epoxybutene recovery.

A final aspect of this invention provides a process for the removal of the water produced as a by-product of the epoxidation reaction. The entire raffinate stream from the extractor, or a fraction thereof, is distilled to remove a distillate product comprising the by-product water of reaction prior to recycle to the absorber. Any water-immiscible extractant present in the raffinate stream will be co-distilled with the by-product water as the extractant/water, minimum-boiling, heterogeneous azeotrope. The distillate is allowed to separate into two liquid phases in a decanter. The aqueous layer may be discarded as waste. The recovered extractant in the organic layer may be recycled to the extractor for reuse.

BRIEF DESCRIPTION OF THE DRAWINGS

The accompanying

FIG. 1 illustrates one embodiment of the process for recovering vaporous epoxybutene from an epoxidation reactor effluent by absorption into an water miscible absorbent, followed by extraction of the epoxybutene into a water-immiscible solvent.

FIG. 2 illustrates another embodiment of the present invention for recovering epoxybutene from a vaporous epoxidation reactor effluent using an water-miscible absorption solvent and subsequent extraction followed by distillation and decantation steps for purification of the recovered epoxybutene and removal of the water produced as a by-product in the epoxidation reaction.

DETAILED DESCRIPTION

Figure 1:
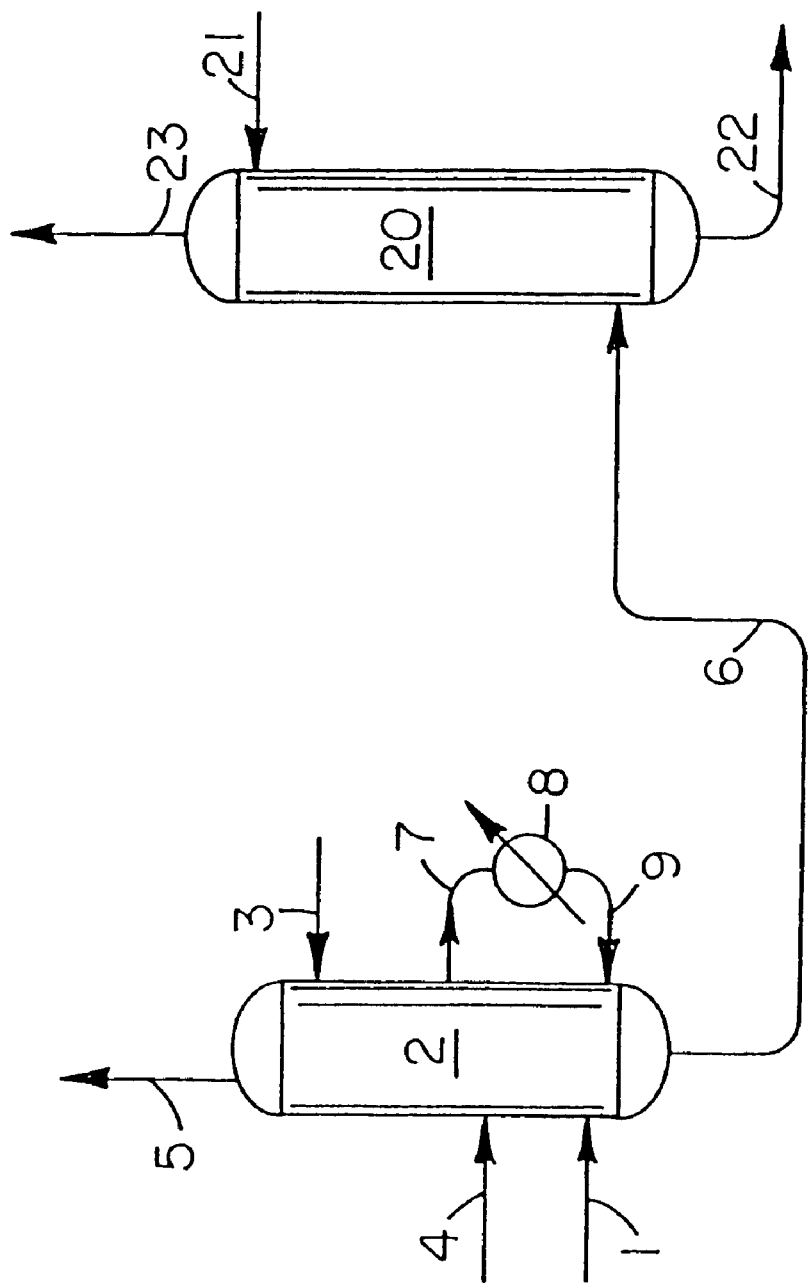
FIGS. 1 and 2 are process flow diagrams illustrating a system embodying the principles of the present invention. While the invention is susceptible to embodiments in various forms, there is shown in the accompanying Figures and hereinafter described in detail preferred embodiments of the invention.

The process of the present invention may be used in combination with any epoxidation process wherein butadiene is contacted with an oxygen-containing gas in the presence of a catalyst to produce an epoxidation effluent comprising epoxybutene, oxygen, unreacted butadiene, and reaction diluent, e.g., nitrogen, carbon dioxide, methane, ethane, propane, n-butane, or other species inert under reaction conditions. The silver-catalyzed, epoxidation processes described in U.S. Pat. Nos. 4,897,498 and 4,950,773 are typical of those that may be employed in the epoxidation zone. The epoxidation zone comprises one or more reactors of any design that allows removal of the heat of reaction in order to prevent an exothermic temperature excursion from occurring. For example, a shell-and-tube design, typically used for ethylene oxide production, may be employed. Other types of reactor designs include multi-staged adiabatic reactors, fluidized bed reactors, moving or transport bed reactors and the like.

The feed to the epoxidation zone comprises butadiene, an oxygen-containing gas and an inert diluent gas in various proportions. Generally, any oxygen ($O_2$) concentration up to the explosive limit can be used. For example, when using nitrogen as the inert gas, the maximum oxygen concentration normally is in the range of about 9 mole percent. Higher oxygen concentration, e.g., up to about 18 mole percent, may be employed using methane as the inert diluent. When using butane as the inert diluent gas, relatively high oxygen concentrations, e.g., up to about 30 mole percent may be employed. The recovery process of the present invention advantageously is used in combination with a butadiene epoxidation process employing carbon dioxide, nitrogen, ethane, or preferably, methane as the inert diluent. The butadiene concentration typically is about 4 to 50 mole percent. The butadiene:oxygen mole ratio in the feed normally is maintained within the range of about 1:5 to 10:1. The inert gas usually constitutes about 25 to 85 mole percent of the total feed to the epoxidation zone. Normally, the feed also includes a small amount, e.g., 1 to 40 parts per million (ppm), of a halide source such as 1,2-dichloroethane. Various other organic halides may be used, many of which are described in U.S. Pat. No. 4,950,773. The concentration of the organic halide in the feed more commonly is in the range of 2 to 10 ppm. The feed also may contain minor amounts, e.g., 5 mole percent or greater, of impurities such as up to about 4 mole percent water and up to 2 mole percent carbon dioxide. Some argon may also be present in the feed. The amount of argon is controlled by purging a small amount of the recycle gas. Typically, the amount of argon is maintained at less than 10 percent.

The gaseous epoxidation effluent typically contains from about 0.5 to about 10 mole percent epoxybutene and preferably from about 1 to 7 mole percent, about 4 to 50 mole percent butadiene, and about 25 to 85 mole percent reaction diluent gas, e.g., nitrogen, carbon dioxide, methane, ethane, propane, n-butane, or other species inert under reaction in the epoxidation zone. As noted above, the diluent gas, for the purpose of the present invention, preferably is carbon dioxide, nitrogen, ethane, or most preferably, methane. The effluent also contains a total of about 0.5 to 10 mole percent of other constituents such as, water, acrolein, furan, vinylacetaldehyde, and crotonaldehyde, formed in the epoxidation reactor. Unconsumed organic halide also is present in the epoxidation effluent. The hot epoxidation effluent, typically 170 to 270° C., more typically 200 to 250° C., may be cooled in a heat exchanger by indirect contact with a suitable cooling media such as water, chilled brine, glycol, or cool reactor feed gas, to a temperature of less than 150° C., preferably less than 100° C.

The absorption zone comprises a columnar, pressure vessel containing trays or a packing material that facilitates intimate gas/liquid contact. The absorption vessel normally is provided with means, such as a disengaging space above the packing, to prevent or minimize entrainment of liquids in the gas stream removed from the upper section thereof. The pressurized, cooled, substantially gaseous, epoxidation effluent is fed to the lower section of the absorption vessel, preferably near the bottom of the vessel. A liquid, water-miscible absorbent is fed to the upper section, preferably near the top, of the absorption vessel and flows downward, thereby absorbing or scrubbing the epoxybutene component from the upwardly-flowing epoxidation effluent. A solution of epoxybutene in the absorbent is removed from the base of the absorption vessel and a vapor comprising butadiene, inert diluent, oxygen and carbon dioxide components of the epoxidation effluent is removed from the top of the vessel.

The liquid, water-miscible absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof and the absorbent compound(s) contain 3 to about 8 carbon atoms. The desirable properties of an absorbent useful in the present invention include: (1) high affinity and capacity for epoxybutene absorption; (2) low specific heat; (3) low of reactivity with epoxybutene and by-products; (4) oxidative stability under absorption and distillation conditions; (5) higher boiling point, e.g., a boiling point of at least about 100° C., preferably at least about 125° C., to reduce losses in absorber off-gas; (6) miscibility with water to allow easy recovery from the absorber off-gas; (7) is a liquid at the normal operating conditions of the recovery process; (8) does not form an azeotrope with epoxybutene or is easily separable from epoxybutene. Although no chemical species possesses all of these desirable characteristics, after extensive testing of candidate absorption solvents, we have found that the classes of compounds set forth above are exemplary solvents for the present invention.

As used herein, the terms "absorbent" and "solvent" are used interchangeably for describing a material or composition that preferentially absorbs epoxybutene from a stream composed of the epoxybutene and other constituents. As used herein, "absorbent zone" and "absorber" are used interchangeably as one skilled in the art will recognize that each performs a substantially similar function and accordingly, will be referred to herein as "absorber". As used herein to describe the absorbents, "water-miscible" refers to liquid absorbent compounds which the absorbent-water binary system does not exhibit liquid-liquid phase formation at the absorption and distillation conditions of this invention. Additionally said absorbent compounds have a normal a boiling point of at least about 100° C., preferably at least about 125° C.

Specific examples of suitable solvents include, but are not limited to, 1-methyl-2-pyrrolidinone (NMP), pyridine, 3-butene-1,2-diol (1,2-diol), propylene glycol, dimethylformamide, dimethylacetamide, diethylformamide, diethylacetamide, acetonitrile, dimethylsulphoxide, morpholine, diethylene glycol dimethyl ether, triethylene glycol dimethyl ether, tetraethylene glycol dimethyl ether, propylene glycol monomethyl ether acetate, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether. The preferred water-miscible solvents are 3-butene-1,2-diol and NMP.

Additionally, the solvent may contain water. The solvent stream in the absorber typically absorbs sufficient water from the epoxidation effluent to induce phase separation of the epoxybutene-rich absorption liquid product. However, separation costs can be minimized by recycling a water-saturated absorption solvent without additional water removal steps. Acceptable water levels in the absorbent may vary depending on factors such as the particular solvent and process operating conditions employed but are between 0.1 and 10 weight percent, preferably between 0.5 and 5 weight percent, based on the weight of the water and water-miscible absorbent.

The absorber and its contents typically are operated at a temperature between about 0 and 100° C. and at a pressure of about 1 to 17 bara, preferably at a temperature from about 5 to 60° C. and pressure of about 2.5 to about 7.5 bara. The amount of liquid absorbent fed to the absorber can vary substantially depending, for example, on the particular vessel configuration, the use of packing material and its type, and the feed rate and composition of the epoxidation effluent. Generally, the molar ratio of the absorbent feed to the total epoxidation effluent feed via line 1 is in the range of about 15:1 to about 1:20, more typically about 3:1 to 1:5. The temperature of the liquid absorbent feed is in the range of about 0 to 100° C., more preferably about 20 to 70° C.

The effluents from the absorption zone comprise (1) a gaseous effluent comprising butadiene, oxygen and an inert diluent which exits the upper section or top of the absorption vessel and (2) a liquid effluent comprising epoxybutene, the absorbent and water which exits the lower section or bottom of the absorption vessel. The amount of epoxybutene present in the gaseous effluent depends on the absorbent flow rate and the number of stages in the absorber but typically is less than 0.1 weight percent, preferably less than about 0.05 weight percent, and more preferably less than about 250 ppm. The gaseous effluent stream may be recycled to the epoxidation zone. When a significant amount of the butadiene present in the absorber feed gas is absorbed by the absorbent employed, additional butadiene may be fed to the absorber so that the butadiene concentration in the gaseous effluent is suitable for recycling to the epoxidation zone. Alternatively, any makeup butadiene required may be fed to the recycle stream at a point downstream from the absorber. Low levels, e.g., less than 500 ppmv, of substantially all oxygen-containing and nitrogen-containing species useful as absorbents in the process of the present invention can cause a reversible decrease in the activity of the silver epoxidation catalyst when present in the recycle gas to the epoxidation zone. The detrimental effect is generally proportional to the level of the absorbent contained in the recycle gas. Thus, it is beneficial to maintain the level of the absorbent in the gaseous effluent from the absorption zone to as low a level as practical and economical. The gaseous effluent which is recycled to the epoxidation zone normally should contain less than 250 ppmv, preferably less than 100 ppmv, of the absorbent used in the absorption zone. One method of minimizing the absorbent level in the recycle gaseous effluent is to use an absorbent that is substantially non-volatile, i.e., has a vapor pressure of less than about 0.033 bar at the temperature and pressure conditions at the top of the absorber. Such substantially non-volatile absorbents typically have normal boiling points in excess of about 210° C. Examples of substantially non-volatile absorbents include diethylene glycol and triethylene glycol. Such a stringent vapor pressure requirement severely and unduly limits the choice of potential solvents to very high-boiling species.

The preferred method of minimizing absorbent content in the recycle gas is to use a water wash step wherein the gaseous effluent is fed to the lower section of a water wash column in order to recover a portion of the vaporized water-miscible absorbent present in the gaseous effluent from the absorber. Water is fed to the upper section of the water wash column and contacts the gaseous absorber effluent countercurrently. The water wash column normally contains a suitable packing material or trays to provide intimate vaporliquid contacting. In this fashion, the water-miscible absorbent content of the gaseous absorber effluent can be reduced easily to less than 100 ppmv, preferably less than 50 ppmv, more preferably less than 25 ppmv. The absorber and water wash column may be two separate pieces of equipment or they may be combined within a single column shell with the upper section of the column separated from the lower section by any appropriate partitioning device known in the art such as a chimney tray with a total liquid draw-off sump. The absorber and water wash column or the single-column combination thereof, also may include a means, such as a disengaging space above the packing, to prevent or minimize entrainment of liquids in the gas stream removed from the upper column section(s).

A liquid effluent comprising water and absorbed water-miscible absorbent is removed from the lower section or bottom of the water wash column. This liquid effluent may be discarded as waste or subjected to further processing for recovery of the water-miscible solvent, e.g., by distillation, or more preferably fed to the upper section of the absorber. A gaseous or vapor effluent comprising butadiene, oxygen and an inert diluent which exits the upper section or top of the water wash may be further processed to remove carbon dioxide before recycling to an epoxidation reactor. Suitable carbon dioxide removal systems are known to those skilled in the art as exemplified by the carbon dioxide removal zones described in U.S. Pat. Nos. 5,117,012 and 5,312,931. Examples of such carbon dioxide scrubbing systems include contacting the carbon dioxide containing stream with an aqueous alkali metal hydroxide, hot potassium carbonate, or aqueous amines in an absorption process known to those skilled in the art.

The separate water-wash step described above may be omitted and the water-miscible absorbent content of the absorber gaseous effluent may be lowered by washing in a carbon dioxide removal zone positioned downstream from the absorber prior to recycling the gas to the epoxidation zone. Suitable carbon dioxide absorbents, i.e., aqueous hot potassium carbonate, aqueous sodium hydroxide, aqueous monoethanolamine, and the like, used in the carbon dioxide removal zone for treatment of the recycle gas, also are capable of absorbing the water-miscible absorbent from the absorber gaseous effluent in a fashion substantially similar to that of a separate water wash column. However, this embodiment is not preferred as the carbon dioxide absorbent becomes contaminated with the water-miscible absorbent and the recovery of the water-miscible absorbent is unduly complicated by such an arrangement.

The liquid effluent comprising epoxybutene, the absorbent and water which exits the lower section or bottom of the absorption vessel normally contains about 1 to 30 weight percent epoxybutene, more typically about 5 to 20 weight percent epoxybutene. This liquid effluent is conveyed to an extraction zone wherein the liquid effluent is contacted with an effective amount of a water-immiscible extractant. As used herein, the term "extractant" is used to describe a material or composition that will preferentially extract a targeted compound, such as epoxybutene, from another stream composed of the targeted compound and other constituents. "Extraction zone" and "extractor" are used interchangeably herein as one skilled in the art will recognize that each performs a substantially similar function and, accordingly, will be referred to herein as "extractor".

The extraction step may be carried out in batch, semi-continuous, or continuous modes of operation. For example, batch operation may comprise charging the aqueous, epoxybutene-rich absorber effluent and an extraction solvent to an extraction zone comprising one or more vessels wherein the two liquids are intimately mixed or agitated to effect mass transfer, and separated into two immiscible liquid phases. One of the resulting liquid phases comprises the extraction solvent containing epoxybutene. The second liquid phase comprising water, the organic absorbent component and some residual epoxybutene may be extracted repeatedly, as needed, to give the desired degree of epoxybutene recovery. After being subjected to extraction, the second phase may be recycled to the absorber. These repeated extraction steps include contacting the aqueous phase with the extraction solvent in a cross-flow, co-current, or countercurrent pattern. Depending on the choice and flow rate of extractant, typically one to 15 theoretical equilibrium extraction stages are required, more typically 2 to 6 stages to achieve the desired degree of epoxybutene recovery.

The extraction process preferably is operated continuously or semi-continuously in a countercurrent manner. This technique, as is well known in the art, can give excellent efficiencies of extraction. See, for example, T. C. Lo, M. H. I. Baird, C. Hanson, *Handbook of Solvent Extraction*, Reprint Edition, Krieger Publishing Company, Malabar, Fla., 1991. Typical countercurrent extraction equipment generally includes columns (agitated and non-agitated), mixer-settlers, and centrifugal extractors. Examples of agitated columns include Karr reciprocating plate, rotating disc, asymmetric disc, Kuhni, York-Scheibel, and Oldshue-Rushton extractors. Examples of non-agitated columns include spray, baffle plate, packed, and perforated plate. Examples of centrifugal extractors include those produced by: Robatel Inc., Pittsfield, Mass.; Westfalia Separator Inc., Northvale, N.J.; and Baker Perkins Inc. (Podbielniak), Saginaw, Mich.

In continuous operation, aqueous epoxybutene-rich absorbent effluent and the extraction solvent are continuously charged to an extraction zone comprising an extractor. The two immiscible phases are intimately contacted in the extractor where they flow countercurrently to one another. The epoxybutene is extracted into the water-immiscible extracting solvent along with some water and butadiene. The organic absorbent component remains largely in the aqueous phase as it passes through the extractor. Depending on the water-immiscible extractant chosen, the composition of the extract and raffinate streams may vary considerably. However, typically the extractant stream comprises 1 to 50 weight percent epoxybutene, 50 to 98 weight percent water-immiscible extractant, 0.5 to 10 weight percent butadiene, less than 10 weight percent water, and less than about 10 weight percent organic absorbent component. More typically, the extractant stream comprises about 5 to 35 weight percent epoxybutene, about 60 to 90 weight percent water-immiscible extractant, 0.5 to 5 weight percent butadiene, 0.5 to 5 weight percent water, and less than about 5 weight percent organic absorbent. The raffinate stream typically comprises less than 0.5 weight percent epoxybutene, preferably less than about 0.1 weight percent, and more preferably less than about 500 ppm by mass of epoxybutene, less than 10 weight percent water-immiscible extractant, 0 to 90 weight percent water, and 10 to 98 weight percent organic absorbent component.

The amount of extraction solvent employed may vary substantially depending, for example, on the identity and composition of the aqueous, epoxybutene-rich absorber effluent, the specific organic absorbent component used, the epoxybutene concentration in the absorber effluent, the extraction solvent being used, the number of equilibrium extraction stages provided in the extraction zone, and the manner in which the extraction process is operated. However, the weight ratio of the extraction solvent to the epoxybutene-rich absorber effluent stream to be extracted normally is in the range of about 10:1 to 0.1:1.

The extraction zone and its contents typically are operated at a temperature between about 0 and 70° C., preferably at a temperature of from about 5 to 50° C. The extraction zone may be operated at any pressure above the bubble point of the streams entering and exiting the extraction zone, preferably at or above about 1.0 bara.

The extraction solvent (extractant) which may be employed in the present invention may be selected from a variety of organic compounds containing 4 to about 25 carbon atoms selected from hydrocarbons, halocarbons, esters, ethers, ketones, and carbonates and mixtures thereof. Generally, the extractant should satisfy four requirements: (1) it should form a separate liquid phase at equilibrium when contacted with a mixture comprising water, epoxybutene and water-miscible absorbent component; (2) it should have a higher selectivity for dissolving epoxybutene than water or the water-miscible absorbent component; (3) it should be separable from epoxybutene by distillation or other means; and (4) it should be inert or substantially inert to reaction with epoxybutene, water, or the water-miscible absorbent component under extraction conditions. The extraction solvent may comprise a mixture of two or more solvents.

Examples of extraction solvents within the scope of this invention include but are not limited to straight- and branched-chain acyclic alkanes containing 4 to 25 carbon atoms; alkenes containing 5 to 25 carbon atoms; cyclic alkanes containing 4 to 5 or 8 to 25 carbon atoms; aromatic hydrocarbons containing 7 to 25 carbon atoms, chloro-, fluoro-, and chlorofluoro-hydrocarbons containing 1 to 25 carbon atoms with boiling points greater than about 0° C.; acyclic ethers containing 6 to 25 carbon atoms; cyclic ethers containing 8 to 25 carbon atoms; acyclic ketones containing 8 to 25 carbon atoms; cyclic ketones containing 10 to 25 carbon atoms; alkyl, alkenyl and aryl esters of alkanoic acids containing a total of about 6 to 25 carbon atoms; alkyl, aryl, and cyclic carbonates containing 4 to 25 carbon atoms.

Specific examples of useful extractants include n-butane, isobutane, isopentane, n-hexane, cyclohexane, heptane, isooctane, n-octane, nonane, decane, undecane, dodecane, Stoddard solvent, cyclopentane, VMP Naphtha, mixed aliphatic hydrocarbons exemplified by ExxonMobil solvents Isopar G, H, L, M, and Ashland Solvent 140, 1,3-butadiene, isoprene, vinylcyclohexene, octenes, nonenes and decenes, limonene, benzene, toluene, p-xylene, m-xylene, o-xylene, mesitylene, 1,3-diisopropylbenzene, 1-methylnaphthalene, 1,2,3,4-tetrahydronaphthalene, carbon tetrachloride, chloroform, 1,2-dichlorobenzene, isobutyl isobutyrate, 2,2,4-trimethyl-1,3-pentandiol diisobutyrate, n-butyl propionate, isobutyl propionate, n-propyl butyrate, isopropyl butyrate, isopropyl isobutyrate, n-butyl butyrate, 2-ethylhexyl acetate, methyl benzoate, isopentyl acetate, pentyl acetate, diisobutyl ketone, and mixtures of any two or more thereof.

If the extraction solvent selected is lower boiling than the dissolved epoxybutene and does not form an azeotrope with epoxybutene, then purified epoxybutene may be recovered from the epoxybutene-rich extraction effluent in the manner described by U.S. Pat. Nos. 5,117,012 and 5,312,931, the disclosure of which is incorporated herein by reference.

Examples of such low-boiling extraction solvents are n-butane, isobutene, and butadiene. For these and similar solvents, the epoxybutene recovery zone comprises a distillation vessel, e.g., a column, a heat source at the base of the vessel, cooling means to condense vapor removed from the top of the vessel and a separator to separate water from the condensed liquid. The extractor effluent comprising the extraction solvent, epoxybutene and minor amounts of butadiene and water may be fed to the mid-section of the epoxybutene recovery column to obtain (1) a gas effluent comprising butadiene from the upper section of the column and (2) a liquid effluent comprising crude epoxybutene from the lower section of the column. The gas effluent contains a minor amount of water that may be removed from the epoxybutene production system by condensing the gas effluent to obtain a two-phase, liquid mixture and separating the aqueous phase from the butadiene phase. Water and the low-boiling water-immiscible extraction solvent typically form a constant minimum-boiling azeotrope mixture. For example, butadiene and water form an azeotrope with a boiling point of approximately 57° C. at 4.46 bars pressure. The water removal may be enhanced by recycling a portion, e.g., up to 80 weight percent, of the condensed extractant phase to the upper section of the epoxybutene recovery vessel. The water-depleted extraction solvent stream removed from the epoxybutene recovery zone may be recycled, directly or indirectly, to the extraction zone along with fresh extraction solvent. The liquid underflow obtained from the epoxybutene recovery zone comprises epoxybutene, typically 90 to 99 weight percent epoxybutene, and minor amounts of extraction solvent, vinyl acetaldehyde, butenediols, vinylcyclohexene, crotonaldehyde and higher boiling impurities. This crude epoxybutene may be further purified by distilling the crude epoxybutene in a distillation column wherein a vapor stream consisting essentially of epoxybutene is removed from the upper section or top of the column and a liquid stream containing most of the impurities is removed from the base of the distillation column.

Referring to accompanying FIG. 1, a cooled epoxidation reactor effluent comprising as majority constituents, epoxybutene, an inert diluent, e.g., nitrogen, carbon dioxide, methane, ethane, propane, n-butane, or other inert material, is fed via line 1 the lower section of an absorber 2. In accordance with the present invention, a water-miscible absorbent is fed to the upper section, preferably near the top, of absorber 2 via line 3. The absorbent flows downward counter-current to the flow of the gaseous effluent entering absorber 2, absorbing or scrubbing the epoxybutene component from the upwardly-flowing epoxidation effluent. The epoxybutene-laden absorbent exits the bottom of absorber 2 via line 6. The scrubbed gaseous effluent exits the top of the absorber via line 5. The overhead stream 5 from the absorber 2 may then be further processed to remove carbon dioxide before recycling to an epoxidation reactor.

Depending on the concentration of epoxybutene in the feed gas of line 1, the temperature of said gas, and the absorbent affinity for butadiene and other constituents of feed gas 1, the heat of absorption may be large and cause a substantial temperature rise across absorber 4. To improve recovery efficiency and lower the ratio of absorbent to feed gas, absorber 4 may be provided with one or more interstage coolers, such as heat exchanger 8 at various places in the column. Liquid is withdrawn via conduit 7 from a tray or sump and diverted through heat exchanger 8, wherein the heat of absorption is removed using methods that are conventional in the art such as by heat transfer against a suitable cooling media, e.g., water, glycol, or chilled brine. The cooled liquid is then returned to absorber 4 via conduit 9 at a point in the column lower than the withdrawal point, typically just one or two stages below the withdrawal point. When advantageous, one or more intercoolers may be placed in the lower section of the column, typically 1 to 4 stages from the bottom. Cooling of absorber 2 also may be provided by flash vaporization of make-up butadiene fed via line 4. In order to generate the cooling effect there must be a significant pressure differential between the make-up butadiene and the operating pressure of the absorber 2. Typically the butadiene must be at least about 2 bars higher pressure than absorber 2.

A liquid stream comprising epoxybutene and water-miscible absorbent is removed from the base of absorber 2 and fed via conduit 6 to extraction zone 20 and wherein the liquid stream is contacted with an effective amount of a water-immiscible extractant entering extraction zone 20 via conduit 21. Within extraction zone 20, the phases of the dispersion are in intimate contact, are optionally agitated to enhance mass transfer, and separated into two immiscible liquid phases. One of the resulting liquid phases, the extract stream 22, comprises the extraction solvent containing epoxybutene. The second liquid phase, raffinate stream 23, which is aqueous and contains the water-miscible absorbent component, may be extracted repeatedly, as needed, to give the desired degree of epoxybutene recovery before the raffinate stream 23 is recycled to absorber 2. The epoxybutene is extracted into the water-immiscible extracting solvent along with some water and butadiene. The organic absorbent component remains largely in the aqueous phase as it passes through the extractor.

When the water-immiscible solvent has a higher density than the aqueous water-miscible solution, conduit 21 should feed the top of extraction zone 20 and conduit 6 should feed the bottom of extraction zone 20. When the water-immiscible solvent has a lower density than the aqueous water-miscible solution, conduit 6 should feed the top of extraction zone 20 and conduit 21 should feed the bottom of extraction zone 20.

Figure 2:
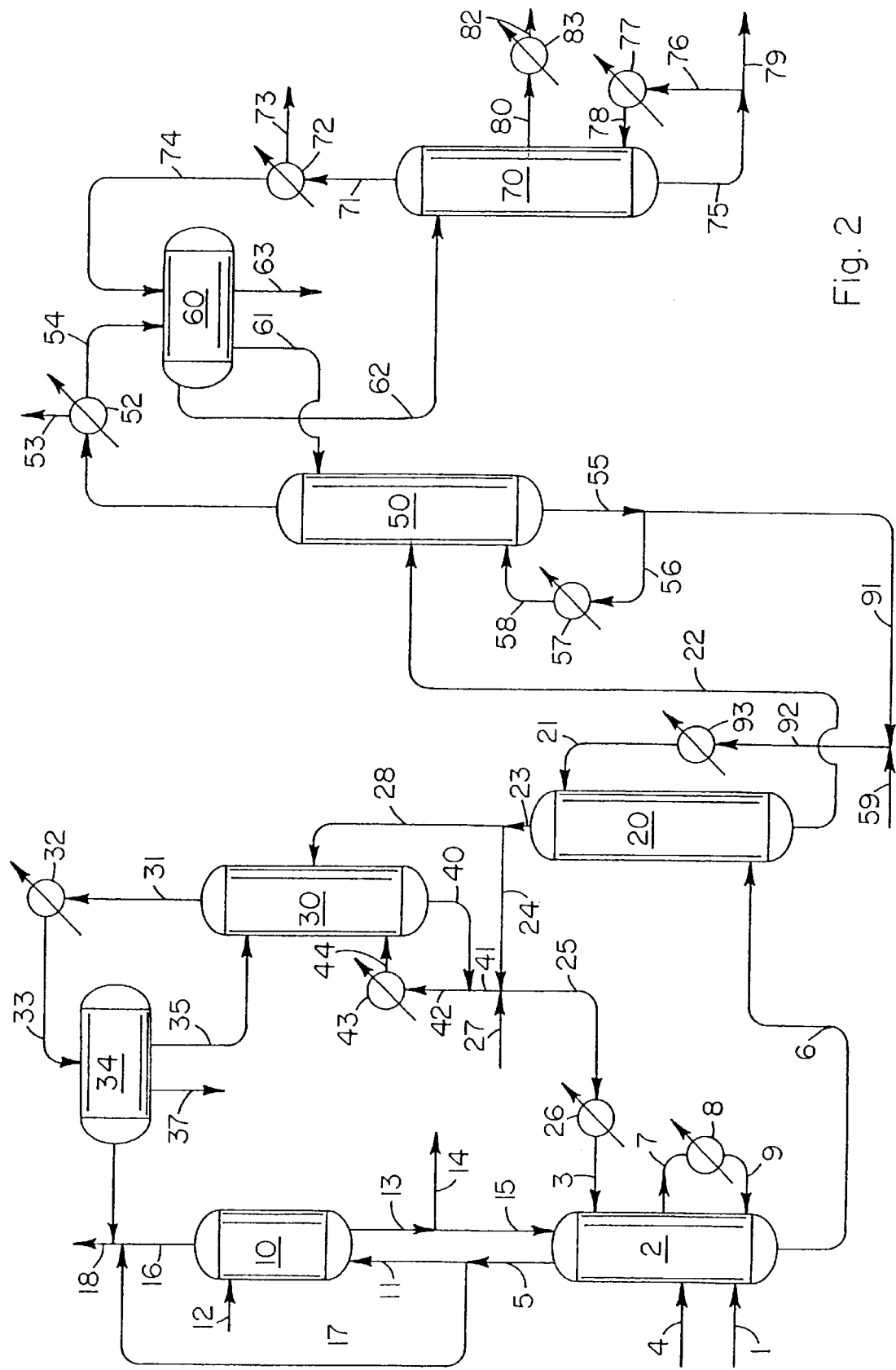

The process flow diagram constituting FIG. 2 schematically illustrates another embodiment of the present invention for the recovery and purification of epoxybutene from a substantially vaporous epoxidation effluent wherein the extraction solvent employed has a boiling point higher than the boiling point of epoxybutene. The streams, conduits and apparatus having numbers 1, 2, 3, 4, 5, 6, 7, 8, 9, 20, 21, 22 and 23 and the operation of the absorber and extraction zones of FIG. 2 are the same as described for FIG. 1 provided that the extraction solvent fed to extraction zone 20 via conduit 21 has a boiling point greater than the boiling point of epoxybutene.

The raffinate stream of conduit 23 may be conveyed in its entirety or partially via conduits 24 and 25 for recycle to absorber 4. If conveyed in its entirety via line 24, then the water produced as a by-product of the epoxidation reactor must be removed at another location, e.g., via line 55 from decanter 50. The temperature of stream 25 is adjusted to the appropriate level by heat exchanger 26 to give the desired temperature of the liquid absorbent feed 3 in the range of about 0 to 100° C., more preferably about 20 to 70° C. Makeup or fresh water-miscible absorbent is added via line 27.

Alternatively, the raffinate stream of conduit 23 may be conveyed either in its entirety or partially via line 28 to water column 30. The purpose of water column 30 is to remove the water produced as a by-product of the epoxidation reactor. Any water-immiscible extractant or epoxybutene present in the raffinate stream will be co-distilled with the by-product water as the extractant/water or epoxybutene/water, minimum boiling, heterogeneous azeotropes. The raffinate is fed by conduit 28 at or above the midpoint e.g., within about three theoretical equilibrium stages from the top, of water column 30. The preferred number of theoretical equilibrium stages in column 30 is 2 to 20 stages, preferably 3 to 8 stages. The temperature at the top stage of the column is normally from about 40 to 100° C., depending on the water content of the overhead vapor. A vaporous distillate is removed from the top of water column 30 through line 31 and is cooled and condensed in heat exchanger 32 by indirect contact with a suitable cooling media such as water, chilled brine, or glycol. The condensed overhead vapors comprising extractant, epoxybutene, and water are conveyed via conduit 33 to reflux decanter tank 34 wherein the distillate is allowed to settle and separate into two phases: an organic phase comprising water-immiscible extractant and epoxybutene and an aqueous phase comprising water. Reflux, comprising a fraction of the top layer of reflux decanter 34, or a fraction of the lower layer of reflux decanter 34, or a fraction of both layers, is provided to column 30 via conduit 35. The preferred reflux ratio is between 0.1 to 5, more preferably 0.3 to 2. The aqueous layer may be discarded as waste via conduit 37 or treated for further recovery of organics. The recovered extractant and epoxybutene in the organic layer may be recycled to extractor 20 for reuse or column 50 via conduit 38 for recovery of epoxybutene.

A liquid comprising water-miscible absorbent and water is removed from the base of water column 30 and is recycled to absorber 2 via conduits 40, 41, and 25, heat exchanger 26 and conduit 3. A portion of the liquid from the base of column 30 is recycled to the lower section of column 30 via lines 40 and 42, heat exchanger (reboiler) 43 and line 44 to provide boilup to column 30. The conditions employed within water column 30 can vary depending on the particular apparatus and absorbent employed. The operating temperature of reboiler 43 normally is within the range of about 100 to 270° C., preferably from about 100 to 220° C. The operating pressure of distillation column 30 normally is within the range of about 0.05 to about 4 bara, and preferably from about 0.3 to about 2.0 bara. Temperatures, pressures, boilup rate are adjusted such that a water balance is maintained in the process.

The epoxybutene-rich extract phase from the extraction zone 20 is conveyed via line 22 to extractant recovery distillation column 50, wherein epoxybutene, water, butadiene, and other light ends, e.g., dissolved oxygen, nitrogen, carbon dioxide, methane or other reaction diluent, are stripped from the water-immiscible extraction solvent. The rich solvent stream 22 is fed to the mid-section, preferably at least 2 theoretical equilibrium stages from the top, of distillation column 50. The section above the feed tray serves as a rectifying section to keep the solvent out of the distillate. The preferred number of theoretical equilibrium stages in column 50 is 4 to 18 stages, preferably 6 to 12 stages. The temperature at the top stage of the column normally is from about 60 to 105° C., depending on the water content of the overhead vapor. A vaporous distillate product comprising epoxybutene, water, butadiene and light ends (low-boiling components) exits the top of column 50 via line 51 and is cooled in partial condenser 52 by indirect contact with a suitable cooling media such as water, chilled brine, or glycol. Light ends, comprising oxygen, nitrogen, carbon dioxide, methane or other reaction diluent, and saturated with butadiene, epoxybutene, and water are removed via line 53.

Typically, it is necessary for economic reasons to recover uncondensed butadiene and epoxybutene contained in the light ends vapor stream 53. One method of recovering this butadiene and epoxybutene is by contact with cooling media at temperatures less than about −10° C. in a heat exchanger. Another method is by vapor recompression followed by heat exchange with a typical cooling media such as cooling water, chilled brine, or glycol. A third and preferred method is absorption in a counter-current absorption tower using a solvent with high affinity for butadiene. It is preferable that the butadiene absorption solvent be the same as either the organic absorbent component used in absorber 2 or the water-immiscible extraction solvent used in extractor 20. The rich solvent containing recovered butadiene and epoxybutene may be sent to absorber 4 or extractor 20 as appropriate, for further processing, the while light end gases may be vented. Specific examples of useful solvents for butadiene recovery in this respect are acetonitrile, N-methylpyrrolidinone, morpholine, dimethylformamide, dimethylacetamide, isopentane, n-hexane, cyclohexane, heptane, isooctane, n-octane, nonane, decane, undecane, dodecane, Stoddard solvent, cyclopentane, VMP Naphtha, mixed aliphatic hydrocarbons exemplified by ExxonMobil solvents Isopar G, H, L, M, and Ashland Solvent 140, isoprene, vinylcyclohexane, octenes, nonenes and decenes, limonene, benzene, toluene, p-xylene, m-xylene, o-xylene, mesitylene, 1,3-diisopropylbenzene, 1-methylnaphthalene, 1,2,3,4-tetrahydronaphthalene, carbon tetrachloride, chloroform, 1,2-dichlorobenzene, isobutyl isobutyrate, 2,2,4-trimethyl-1,3-pentandiol diisobutyrate, n-butyl propionate, isobutyl propionate, n-propyl butyrate, isopropyl butyrate, isopropyl isobutyrate, n-butyl butyrate, 2-ethylhexyl acetate, methyl benzoate, isopentyl acetate, pentyl acetate, diisobutyl ketone, and mixtures or any two or more thereof. The means for the recovery of butadiene described above are not shown in FIG. 2.

The condensed overhead vapors comprising epoxybutene, water and minor amounts of butadiene are conveyed via conduit 54 to reflux decanter tank 60 wherein the distillate is allowed to settle and separate into two phases. The liquid within line 54 preferably comprises about 9 to 70 weight percent water and 30 to 91 weight percent epoxybutene. The organic phase within decanter 60 typically comprises about 92 to 98 weight percent epoxybutene, about 2 to 3 weight percent water, and butadiene.

The aqueous phase typically comprises about 95 to 97 weight percent water and 3 to 5 weight percent epoxybutene. Reflux, comprising a fraction of the top layer of reflux decanter 60, or a fraction of the lower layer of reflux decanter 60, or a fraction of both layers, is provided to column 50 via conduit 61. The preferred reflux ratio is between 0.5 to 5, more preferably 1 to 2.5, and is adjusted to give the preferred epoxybutene composition range in the condensed vapors of conduit 54. The water-rich lower liquid phase from decanter 60 may be conveyed via line 63 to water removal column 30 or, preferably, to extractor 20 for further recovery of the epoxybutene contained therein.

A liquid comprising epoxybutene-lean, water-immiscible extraction solvent and is removed from the base, i.e., the lower section or bottom, of extractant recovery column 50 through conduit 55 and is returned to extraction zone 20 via conduits 91 and 92, heat exchanger 93 and conduit 21. A portion of the liquid in conduit 55 is recycled to the lower section of column 50 via line 56 heat exchanger (reboiler) 57 and line 58 to provide boilup to column 50. The conditions employed within the extractant recovery column 50 can vary depending on the particular apparatus and extractant employed. The operating temperature of reboiler 57 normally is within the range of about 100 to 270° C., preferably from about 100 to 220° C. The operating pressure of the distillation column 40 normally is within the range of about 0.1 to about 4 bara, and preferably from about 0.3 to about 2.0 bara. Temperatures, pressures, and/or boilup rate are adjusted such that the lean solvent stream 55 from the base of column 50 comprises less than 0.5 weight percent, preferably less than 500 ppm by mass, more preferably less than 100 ppm by mass of epoxybutene.

Stream 92 may be heat-interchanged with stream 22 to improve the energy efficiency of the process. A fraction, i.e., generally less than 0.1 per cent of stream 91 may be purged from the process prior to interchange to prevent the build-up of high-boiling, water-immiscible impurities. Make-up or fresh water-immiscible solvent may be supplied via line 59. The temperature of stream 91 is adjusted further by heat exchanger 93 to about 0 to 70° C., more preferably about 5 to 50° C., the desired temperature of the water-immiscible extractant feed to extraction zone 20.

The epoxybutene-rich upper liquid phase from decanter 60 is conveyed via line 62 to epoxybutene purification column 70, wherein water and any remaining butadiene are stripped from epoxybutene. The aqueous epoxybutene stream 62 is fed near the top, i.e., within about three theoretical equilibrium stages from the top, of distillation column 70. The preferred number of theoretical equilibrium stages in column 70 is 4 to 20 stages, preferably 6 to 15 stages. The temperature at the top stage of the column is normally from about 60 to 75° C., depending upon the water content of the overhead vapor. A vaporous distillate product exits the top of column 70 via line 71 and is cooled in partial condenser 72 by indirect contact with a suitable cooling media such as water, chilled brine, or glycol. Light ends, comprising oxygen, nitrogen, carbon dioxide, methane or other reaction diluent, and saturated with butadiene, epoxybutene, and water are removed via line 73. Butadiene and epoxybutene may be recovered from conduit 73 by the same means described above concerning stream 53. The condensed overhead vapors comprising epoxybutene and water are conveyed via conduit 74 to reflux decanter tank 60 wherein the distillate is allowed to settle and separate into two phases. The composition of the vapor of line 71 typically is on the epoxybutene-rich side of the epoxybutene-water minimum-boiling azeotrope, and typically comprises about 1 to 8 weight percent water and greater than about 90 weight percent epoxybutene. Condenser 52 and condenser 72 serve essentially the same function and, in order to save capital expense, may be physically the same piece of equipment if so desired.

A liquid product comprising epoxybutene and less than 0.1 weight percent, preferably less than 500 ppm by mass, more preferably less than 150 ppm by mass of water is removed from the base of column 70 through conduit 75. A portion of the liquid in conduit 75 is recycled to the lower section of column 70 via line 76, heat exchanger (reboiler) 77 and line 78 to provide boilup to column 70. The conditions employed within epoxybutene recovery column 70 can vary depending on the particular apparatus employed. The operating temperature of reboiler 77 normally is within the range of about 67 to 120° C., preferably from about 67 to 100° C. The operating pressure of the distillation column 60 is normally within the range of about 1 to about 4 bara, and preferably from about 1 to about 2.3 bara. Temperatures, pressures, and boilup rate are adjusted such that the dehydrated epoxybutene product of lines 75 and 79 from the bottom of column 70 comprises less than 0.1 weight percent, preferably less than 500 ppm by mass, more preferably less than 150 ppm by mass of water. Optionally, product epoxybutene may be withdrawn as a vapor or liquid side draw via line 80, above, e.g., at least 1 theoretical stage above, reboiler 77. If stream 80 is withdrawn as a vapor, heat exchanger 81 acts as a condenser. If stream 80 is a liquid, then stream 80 may be cooled by exchanger 81. When epoxybutene product is withdrawn via sidedraw 80 and conduit 82, stream 75 typically comprises epoxybutene, higher boiling epoxybutene oligomers, extractant, and 3-butene-1,2-diol by-products. It is possible to achieve epoxybutene product purities of greater than 99 weight percent or even greater than 99.5 weight percent from either line 82 or line 75.

As mentioned above, low levels, e.g., less than 500 ppmv, of substantially all oxygen-containing and nitrogen-containing species useful as epoxybutene absorbents in absorber 2 may cause a reversible decrease in the activity of the silver epoxidation catalyst when present in the recycle gas to the epoxidation zone. In the embodiment of FIG. 2, vapor effluent 5 is conveyed from absorber 2 via lines 5 and 11 to the lower section of water wash column 10 in order to recover a portion of the vaporized, water-miscible absorbent present in stream 5. Water is fed to water wash column 10 through conduit 12 wherein it contacts countercurrently the vapor fed by conduit 11 to absorber 10, which contains a suitable packing material or trays to provide intimate vapor/liquid contacting. In this fashion, the water-miscible solvent content of the off-gas removed from column 10 via line 16 can be reduced easily to less than 100 ppmv, preferably less than 50 ppmv, more preferably less than 25 ppmv. A liquid comprising water and absorbed water-miscible epoxybutene solvent is removed from the base of water wash column 10 via line 13 and may be fed to the upper section of absorber 2. Alternatively, the liquid removed from the base of water wash column 10 can be discarded as waste or removed separately from column 10 via conduits 13 and 14 for recovery of the water-miscible solvent by other means, e.g., distillation. The overhead vapor contained in conduit 16 from the water wash column 10 may be further processed to remove carbon dioxide before recycling to an epoxidation reactor.

Optionally, some or all of the vapor effluent from absorber 2 may by-pass water-wash column 10 via conduit 17 and the water-miscible solvent content of streams 17 and 18 may be lowered by washing in any carbon dioxide removal zone downstream from the absorber 2 prior to recycling the gas to the epoxidation zone. However, this embodiment is not preferred as the carbon dioxide absorbent becomes contaminated with the water-miscible EpB absorbent and the recovery of the water-miscible EpB solvent is unduly complicated by such an arrangement.

Although absorber 2 and water wash column 10 are illustrated as two separate pieces of equipment, it is contemplated to be within the scope of the present invention, and one skilled in the art will understand, that columns 2 and 10 may be combined within a single column shell if desired with the upper section of the column separated from the lower section by any appropriate partitioning device known in the art such as a chimney tray with a total liquid draw-off sump. Absorber 2 and water wash column 10 or the single-column embodiment therein, may also include a means, such as a disengaging space above the packing, to prevent or minimize entrainment of liquids in the gas stream removed from the upper column section(s).

Absorber 2, water wash column 10, water column 30, solvent recovery column 40, and epoxybutene column 70 of the first and second embodiments of this invention typically comprise columnar, pressure vessels containing trays or a packing material that facilitates intimate gas/liquid contact. The gas/liquid contacting equipment in the columns may include, but is not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings™. These and other types of suitable gas/liquid contacting equipment are described in detail in Kister, H. Z. Distillation Design, McGraw-Hill, N.Y. (1992), Chapters 6 and 8 the disclosures of which are incorporated herein by reference.

To prevent the formation of butadiene polymerization products in either the first or second embodiments of this invention, absorption of epoxybutene in absorber 2, extractant recovery column 50, and epoxybutene column 70 may be carried out in the presence of a polymerization inhibitor known to those skilled in the art. For example, suitable polymerization inhibitors include tertiary butyl catechol or amine oxide compounds. The polymerization inhibitor may be added to the upper section of the absorber column 2, extractant recovery column 50, and epoxybutene column 70. The formation of low molecular weight, butadiene polymerization products are substantially suppressed by the addition of about 300 to 400 ppm inhibitor, based on the amount of vapor removed from the column. The inhibitor addition point can be any place that is convenient for the operation of columns 2, 50, and 70 by means of a low-flow addition device such as a syringe pump.

Epoxybutene reacts readily with nucleophiles such as water and alcohols to form 3-butene-1,2-diol and glycol ethers, respectively. However, the relative rate of epoxybutene reaction with nucleophiles is a function of pH. Epoxybutene, like other epoxides, undergoes both acid and base catalysis. Acid catalysis has the larger influence on the rate of reaction. For example, the rate of epoxybutene hydrolysis is over 500 times greater at pH 3 than at pH 7. At pH 11, the rate is over 17 times greater than at pH 7. Since it is desirable to minimize epoxybutene losses due to reaction with nucleophiles, EpB reactivity can be reduced by maintaining the epoxybutene-laden solution at or near a pH of about 7 to 8. This can be done by adding a basic compound to the recovery system. Generally the process gas from the reactor contains ppm levels of formic acid and other organic acids. Thus, any basic material which is capable of neutralizing organic acids may be used in the present process. Examples include Group Ia (alkali) metal hydroxides, bicarbonates, carbonates, and phosphates; Group IIa (alkali earth) metal hydroxides and carbonates; ammonia; ammonium hydroxide, bicarbonate, carbonate, and phosphate; amines such as tertiary amines, e.g., trialkyl amines containing up to about 18 carbon atoms; amino alcohols, such as tertiary aminoalkanols, e.g., N,N-dialkylaminoalkanols containing up to about 20 carbon atoms; basic ion-exchange resins, and similar materials. The use of phosphate buffers, ammonia, ammonium buffers, and/or alkyl amines are the preferred methods.

The buffer component or components typically are added to the absorption/distillation system as an aqueous mixture on an as needed basis to maintain the pH within the proper range. The buffer solution may be added to any or all of following locations or other convenient addition locations as needed: absorber 2, water column 30, water-wash column 10, extractant recovery column 50, decanter 60 and/or epoxybutene column 70.

EXAMPLES

The process provided by the present invention is further illustrated by the following examples. All percentages given in the examples are by weight unless specified otherwise.

Example 1

This example compares the extraction affinity of various water-immiscible solvents for epoxybutene in the presence of aqueous absorbent mixtures, as occurs in the extraction zone of both embodiments of this invention. A standard mixture of 35% water and 65% 3-buten-1,2-diol (diol) was prepared. Epoxybutene was added to the standard solution to give a composition comprising approximately 10 weight percent epoxybutene. For each candidate extractant solvent specified in Table 1, one part by weight water-immiscible solvent was added to one part standard water-diol-epoxybutene solution in a separatory funnel. The mixture was vigorously shaken, allowed to settle, then separated into two liquid phases at room temperature. The aqueous and organic layers from the decantation were analyzed by gas chromatography to determine the composition of each layer. From these compositions, distribution coefficients were calculated for epoxybutene, water, diol, and the candidate extractant as follows:

$$\text{Distribution coefficient} = \frac{\text{Mass of component } i \text{ in organic layer}}{\text{Mass of component } i \text{ in aqueous layer}}$$

Preferred solvents form two liquid phases with the standard solution and have a high distribution coefficient for epoxybutene and extractant, and low distribution coefficients for water, and diol. Distribution coefficients for epoxybutene, water, diol, and water-immiscible solvent are given in Table I.

TABLE I

| | Distribution Coefficients | | | |
|---|---|---|---|---|
| Solvent | Epoxy-Butene | Water | Diol | Solvent |
| n-Decane | 1.06 | 0.000 | 0.001 | 1907 |
| Toluene | 4.15 | 0.003 | 0.010 | 52 |
| Isobutyl isobutyrate | 3.49 | 0.022 | 0.065 | 34.4 |
| n-Butanol | ONE PHASE | | | |
| Cyclohexanone | ONE PHASE | | | |
| Methyl Isobutyl Ketone | ONE PHASE | | | |
| 2-Methoxy-1-Methylethyl Acetate | ONE PHASE | | | |
| Methyl t-Butyl Ether | ONE PHASE | | | |
| Dimethylsulfoxide | ONE PHASE | | | |
| Isophorone | ONE PHASE | | | |
| 2-Ethylhexanol | ONE PHASE | | | |
| Propylene Carbonate | ONE PHASE | | | |
| 1,3-Diisopropylbenzene | 1.92 | 0.001 | 0.004 | 329 |
| 1-Methylnaphthalene | 3.10 | 0.002 | 0.006 | 101 |
| ISOPAR H | 1.14 | 0.000 | 0.001 | 6404 |
| Mixed Dimethyl Heptanones | 3.73 | 0.021 | 0.079 | 47.4 |
| Ashland 140 Solvent | 0.84 | 0.001 | 0.001 | 2887 |
| 3-Pentanol | ONE PHASE | | | |
| Chloroform | 8.73 | 0.024 | 0.106 | 8.33 |
| m-Xylene | 2.32 | 0.002 | 0.005 | 1479 |
| 2,2,4-Trimethyl-1,3-Pentanediol Diisobutyrate | 2.19 | 0.012 | 0.027 | 124 |
| 1,2-Dichlorobenzene | 3.91 | 0.002 | 0.007 | 54.4 |
| p-Xylene | 4.34 | 0.002 | 0.005 | 368 |
| Butyl Propionate | 3.96 | 0.042 | 0.115 | 14.1 |
| Methyl Benzoate | 2.84 | 0.076 | 0.155 | 6.66 |
| 1,2,3,4-Tetrahydronaphthalene | 1.91 | 0.010 | 0.021 | 51.8 |
| n-Heptane | 1.93 | 0.001 | 0.001 | 851 |
| 2-Pentanone | ONE PHASE | | | |
| Cyclohexane | 2.09 | 0.001 | 0.000 | 215 |
| VMP Naptha | 0.92 | 0.000 | 0.001 | 3805 |
| 3-Pentanone | ONE PHASE | | | |
| Isopentyl Acetate | 2.80 | 0.073 | 0.181 | 25.6 |
| Limonene | 2.28 | 0.001 | 0.003 | 352 |

Example 2

This example illustrates the efficacy of a solvent mixture comprising NMP and water for epoxybutene absorption from the product gas of an epoxidation reaction zone. The embodiment of this process as practiced in this example is shown in FIGS. 1 and 2. After partial removal of carbon dioxide, the off-gas from epoxybutene absorber 2 passed through an epoxidation zone comprising two identical stainless steel tubes, 7.62 meters tall, 18.7 mm inside diameter, packed with 1.2 meters of Denstone ceramic packing on top of 3 meters of silver/cesium/alumina catalyst rings. The epoxidation zone was maintained at an average maximum temperature of about 240° C. at an inlet pressure of about 5.25 bar (76 psia).

The epoxidation catalyst employed comprised an alumina support in the form of 6 mm outside diameter rings having deposited thereon 12 weight percent silver and 700 parts per million by weight (ppmw) cesium. The catalyst was prepared according to known procedures, i.e., as exemplified by U.S. Pat. No. 4,897,498, by impregnating the support material with solutions of a silver amine salt and cesium chloride followed by a thermal decomposition/reduction treatment in the presence of an oxygen-containing gas to convert the silver salt to silver metal.

An epoxybutene-laden reactor product gas, at an average rate of 140 to 300 standard liters per minute, with average composition comprising about 12 mole percent oxygen, 12 mole percent 1,3-butadiene, 63 mole percent methane, 2–4 ppmv ethylchloride, 20 ppm trimethylamine, 4 mole percent carbon dioxide, and 5 mole percent nitrogen and argon was cooled to about 34° C. This gas was fed by conduit 1 to the lower section of epoxybutene absorber 2 comprising a stainless steel column, 83 mm inside diameter, packed with about 1.8 meters of 9.5 mm stainless steel Penn State packing. A mixture comprising 93% NMP, 1% 1,2-diol, 1% oligomers, and 5% water was fed at a rate of about 11 liters per hour to the upper section of the absorber via conduit 3. The absorbent feed temperature was maintained at about 29° C. by heat exchange against cooling water. The absorber operated at an outlet pressure about 4.5 bar absolute, with an average temperature of about 30° C. The epoxybutene concentration in the off-gas of line 5 from the epoxybutene absorber was below detection limits. Approximately 60% of the butadiene in the reactor product gas 1 was absorbed along with the epoxybutene. To maintain the proper butadiene concentration in off-gas of conduit 5, fresh butadiene was added via conduit 4 at a rate of about 1000 g/hour to epoxybutene absorber 2. Absorption of trimethylamine from the reactor product effluent was sufficient to maintain the pH of the epoxybutene-rich absorbent at a value of about 8 to 9.

Example 3

This example illustrates the efficacy of a solvent mixture comprising 1,2-diol and water for epoxybutene absorption from the product gas of an epoxidation reaction zone. The embodiment of this process as practiced in this example is shown in FIGS. 1 and 2. The reactor system described for Example 2 was used for Example 3.

An epoxybutene-laden reactor product gas, at an average rate of 140 to 300 standard liters per minute, with average composition comprising about 12 mole percent oxygen, 12 mole percent 1,3-butadiene, 63 mole percent methane, 2–4 ppmv ethylchloride, 20 ppmv trimethylamine, 4 mole percent carbon dioxide, and 5 mole percent nitrogen and argon was cooled to about 34° C. This gas was fed by conduit 1 to the lower section of epoxybutene absorber 2 comprising a stainless steel column, 83 mm inside diameter, packed with about 1.8 meters of 9.5 mm stainless steel Penn State packing. A mixture comprising 85% 1,2-diol, 5% oligomers, and 10% water was fed at a rate of about 14 liters per hour to the upper section of the absorber via conduit 3. The absorbent feed temperature was maintained at about 29° C. by heat exchange against cooling water. The absorber operated at an outlet pressure of about 4.5 bara, with an average temperature of about 30° C. The epoxybutene concentration in the off-gas removed through line 5 from the epoxybutene absorber averaged about 200 to 500 ppm. Approximately 35% of the butadiene in the reactor product gas 10 was absorbed along with the epoxybutene. To maintain the proper butadiene concentration in the off-gas of line 5, fresh butadiene was added at a rate of about 700 g/hour to epoxybutene absorber 2. Absorption of trimethylamine from the reactor product effluent was sufficient to maintain the pH of the epoxybutene-rich absorbent at a value of about 8 to 9.

Example 4

The extraction of epoxybutene from an absorbent mixture of 1,2-diol and water was demonstrated in a two-stage cross-flow mode with p-xylene as the extractant. A feed mixture generated in the fashion of Example 3, weighing 1498.6 grams and comprised of 13.6% epoxybutene, 55.8% water, and 30.6% 1,2-diol was mixed vigorously with 1498.6 grams of p-xylene extractant solvent in a four-liter separatory funnel. The contents of the funnel were allowed to settle for 30 minutes and the lower and upper layers were separated. The aqueous layer of 1332 grams was mixed with 1392 grams of fresh p-xylene in a four-liter separatory funnel. The contents of the funnel were allowed to settle for 30 minutes and the lower and upper layers were separated. The combined layers from the two cross-flow extraction stages weighed 3028.5 grams and comprised 6.6% epoxybutene, >0.1% water, 0.3% 1,2-diol, and 93.1% p-xylene. The aqueous layer from the second stage of the cross-flow extractions weighed 1347.7 grams and comprised >3900 ppm by mass epoxybutene, 65% water, 34.6% 1,2-diol, and <100 ppm by weight p-xylene. Approximately 97.4% of the epoxybutene in the original feed mixture was recovered in the combined p-xylene extract phases.

Example 5

The extraction of epoxybutene from an absorbent mixture of 1,2-diol and water was demonstrated in a two-stage cross-flow mode using isobutyl isobutyrate as the extractant. A feed mixture generated in the fashion of Example 3, weighing 1350 grams and comprised of 9% epoxybutene, 52.1%, and 38.9% 1,2-diol was mixed vigorously with 1351.2 grams of isobutyl isobutyrate extractant solvent in a four-liter separatory funnel. The contents of the funnel were allowed to settle for 30 minutes and the lower and upper layers were separated. The aqueous layer of 1208.9 grams was mixed with 1222.1 grams of fresh isobutyl isobutyrate in a four-liter separatory funnel. The contents of the funnel were allowed to settle for 30 minutes and the lower and upper layers were separated. The combined layers from the two cross-flow extraction stages weighed 2764.13 grams and comprised 4.3% epoxybutene, >0.6% water, 1.8% 1,2-diol, and 93.4% isobutyl isobutyrate. The aqueous layer from the second stage of the cross-flow extractions weighed 1158.8 grams and comprised >2100 ppm by mass epoxybutene, 53%, 46% 1,2-diol, and <5000 ppm by weight isobutyl isobutyrate. Approximately 97.2% of the epoxybutene in the original feed mixture was recovered in the combined extract phases.

Comparative Example 1

A mixtures comprising 45.4% water, 9.1% epoxybutene, and 45.5% 3-butene-1,2-diol (1,2-diol) was distilled continuously to demonstrate the recovery of epoxybutene from a solvent mixture by distillation. The distillation was conducted in a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. The bottoms product was cooled in a small water-chilled stainless steel heat exchanger placed in line on the suction side of the pump. The distillate product flowed by gravity to a jacketed cooled receiver, which also functioned as a phase decanter. Thermocouples were provided at the reboiler, and distillation head. The continuous run lasted about 12 hours in duration with a total feed of about 1192 grams. A reflux ratio of 1:1 was employed. The column was operated at about 1 bar absolute pressure. During steady state operation the average distillate composition comprised about 16% water, 84% epoxybutene, and less than 0.01% 1,2-diol. The distillate separated into two liquid phases upon settling. The average bottoms product comprised 59.2% water, less than 0.2% epoxybutene, and 39.9% 1,2-diol. Approximately 66% of the epoxybutene present in the feed reacted to form 1,2-diol and higher diol oligomers and 93% of the unreacted epoxybutene was recovered in the distillate. This example clearly shows that epoxybutene is highly susceptible to hydrolysis during distillation in the presence of high concentrations 1,2-diol and water.

Example 6

The combined organic layers from the cross-flow extraction of Example 4 comprising 6.6% epoxybutene, >0.1% water, 0.3% 1,2-diol, and 93.1% p-xylene was distilled continuously to demonstrate the recovery of epoxybutene from an extractant by distillation. The distillation was conducted in a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. The product removed from the base of the column was cooled in a small water-chilled stainless steel heat exchanger placed in line on the suction side of the pump. The distillate product flowed by gravity to a jacketed cooled receiver, which also functioned as a phase decanter. Thermocouples were provided at the reboiler, and distillation head. The continuous run lasted about 10 hours in duration with a total feed of about 3028 grams. A reflux ratio of 3:1 was employed. The column was operated at about 1 bar absolute pressure. During steady state operation the average distillate composition comprised about 20.4% water, 79.4% epoxybutene, and less than 0.2% 1,2-diol. The distillate formed two liquid phases upon settling. The average bottoms product comprised 600 ppm by mass water, less than 300 ppm by mass epoxybutene, 0.65% 1,2-diol and other high boilers, and 99.2% p-xylene. Less than 0.5% of the epoxybutene present in the feed reacted to form 1,2-diol and higher diol oligomers and 99.5% of the unreacted epoxybutene was recovered in the distillate. This example clearly shows that epoxybutene losses can be greatly reduced by extraction of epoxybutene from the aqueous absorbent before distillative recovery of epoxybutene.

Example 7

The combined organic layers from the cross-flow extraction of Example 5 comprising 4.3% epoxybutene, >0.6% water, 1.8% 1,2-diol, and 93.4% isobutyl isobutyrate was distilled continuously to demonstrate the recovery of epoxybutene from an extractant by distillation. The distillation was conducted in a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. The product recovered from the base of the column was cooled in a small water-chilled stainless steel heat exchanger placed in line on the suction side of the pump. The distillate product flowed by gravity to a jacketed cooled receiver, which also functioned as a phase decanter. Thermocouples were provided at the reboiler and distillation head. The continuous run lasted about 8 hours in duration with a total feed of about 2764 grams. A reflux ratio of 3:1 was employed. The column was operated at about 1 bar absolute pressure. During steady state operation the average distillate composition comprised about 11.5% water, 86.4% epoxybutene, less than 0.3% 1,2-diol, and 1.7% isobutyl isobutyrate. The distillate formed two liquid phases upon settling. The average bottoms product, i.e., the liquid product recovered from the base of the column, comprised 1700 ppm by mass water, less than 500 ppm by mass epoxybutene, 0.05% 1,2-diol and 99.7% isobutyl isobutyrate. Less than 0.4% of the epoxybutene present in the feed reacted to form 1,2-diol and higher diol oligomers and 99.0% of the unreacted epoxybutene was recovered in the distillate. This example clearly shows that epoxybutene losses can be greatly reduced by extraction of epoxybutene from the aqueous absorbent before distillative recovery of epoxybutene.

Examples 8–10

Epoxybutene-rich distillate layers produced in the manner described in Example 6 were distilled to demonstrate epoxybutene recovery in a distillation system consisting of a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. Since the feed mixture comprised little water, the pH of the feed mixture was not measured, nor was any buffer solution added.

The product removed from the base of the column was cooled in a small water-chilled stainless steel heat exchanger placed in line on the suction side of the pump. The distillate product flowed by gravity to a jacketed cooled receiver, which also functioned as a phase decanter. For all examples a reflux ratio of 1:1 was employed. Thermocouples were provided at the reboiler and distillation head. Each continuous run lasted from eight to 12 hours in duration. Feed compositions and conditions for each example are given in Table II. In all examples the distillate separated into two phases upon standing. This two-phase mixture was decanted and stored separately as water-rich and epoxybutene layers.

All sampled were analyzed by gas chromatography using a thermal conductivity detector. Mass balances were performed to determine percent distillate, distillate and bottoms compositions, percent epoxybutene loss, the recovery of unreacted epoxybutene, and oligomer make-rate. Mass balance and temperature data are presented in Table III. The following terms used in Tables II and III are defined herein as follows: Percent Distillate is the total mass of distillate collected divided by the total mass of material fed to the column×100 and Percent Epoxybutene Loss is the sum of the mass of epoxybutene collected in the distillate and the mass of the epoxybutene collected in the liquid column base product divided by the total mass of epoxybutene fed to the column×100; The Oligomer Make-Rate, the sum of the mass of oligomer in the distillate and the mass of oligomer collected in the liquid column base product divided by the mass of the epoxybutene lost×100. The oligimer make rate for Example 10 was 4.2% of the EpB loss. However, the oligimer make rate for Examples 8 and 9 was undetectable.

In Table II, the feed temperature (Temp) is given in °C., the pressure (Press) within the column is given in Torr, the total material fed (Total Feed) is given in grams and the composition of the feed is given as a weight percentage. In Table III, the temperature at the head or top of the column (Head Temp) and at the column reboiler (Reboiler Temp) are given in °C., and the compositions of the distillate and bottoms liquid are given as weight percentages.

TABLE II

| | | | | | Feed Composition | | | |
|---|---|---|---|---|---|---|---|---|
| Example | pH | Press | Temp | Total Feed | Water | 1,2-Diol | Epoxy-Butene | Oligomer |
| 8 | 5 | 736 | 65.3 | 2600.4 | 2.1 | 0.0 | 97.9 | 0 |
| 9 | 5.5 | 738 | 65.8 | 2611.0 | 2.0 | 0.01 | 98.0 | 0 |
| 10 | 5 | 738 | 66.2 | 4759.3 | 2.1 | 0.08 | 97.8 | 0 |

TABLE III

| | | | | Distillate Composition | | | Bottoms Composition | | | | Epoxy-Butene Loss |
|---|---|---|---|---|---|---|---|---|---|---|---|
| Example | Top Temp | Reboiler Temp | Percent Distillate | Water | 1,2-Diol | Epoxy-Butene | Water | 1,2-Diol | Epoxy-Butene | Oligomer | |
| 8 | 63.6 | 68.6 | 38.16 | 4.9 | — | 94.9 | 0.01 | 0.04 | 99.92 | — | 0.02 |
| 9 | 62.5 | 68.6 | 42.7 | 5.0 | — | 95.0 | 0.02 | 0.08 | 99.84 | — | 0.04 |
| 10 | 64.8 | 69.0 | 70.61 | 2.8 | <0.01 | 97 | 0.04 | 0.50 | 99.4 | <0.01 | 0.052 |

Example 11

A water-rich distillate layer generated in the manner described in Examples 2–7 was distilled to demonstrate epoxybutene removal in a distillation system consisting of a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed to the column was supplied from a 5-liter jacketed vessel via a piston pump and bottoms take-off was removed via a second piston pump. A total of 2579.1 g of feed material consisting of 96.92% water, 0.09% 1,2-diol, 3.0% epoxybutene and no oligomer was fed at a temperature of 99.3° C. The pH of the feed mixture was adjusted to a value of 8 by the addition of a $K_2CO_3$—$H_3PO_4$ buffer solution. A reflux ratio of 1:1 was employed for this example. The pressure within the distillation column was 740 Torr.

The bottoms product (pH=9.5–10) was cooled in a small, water-chilled, stainless steel heat exchanger placed in line on the suction side of the pump. The distillate product flowed by gravity to a jacketed cooled receiver, which also functioned as a phase decanter. Thermocouples provided at the reboiler and distillation head showed a head temperature of 96.7° C. and a reboiler temperature of 102.1° C. The continuous run was 12 hours in duration. The distillate separated into two phases upon standing. This two-phase mixture was decanted and stored separately as water-rich and epoxybutene layers.

All samples were analyzed by gas chromatography using a thermal conductivity detector. A mass balance was done to determine percent distillate, distillate and bottoms compositions, percent epoxybutene loss, the recovery of unreacted epoxybutene, and oligomer make-rate. The composition of the distillate was 23.9% water, 0.08% 1,2-diol and 76.0% epoxybutene and the composition of the bottoms liquid was 99.9% water and 0.1% 1,2-diol. The percent epoxybutene loss was 1.5%.

The invention has been described in detail with particular reference to preferred embodiments thereof, but it will be understood that variations and modifications can be effected within the spirit and scope of the invention.

We claim:

1. Process for the recovery of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises the steps of:
   I. feeding the effluent to an absorption vessel wherein the effluent is intimately contacted with a water-miscible, liquid absorbent to obtain:
      (i) a gaseous effluent comprising butadiene, oxygen and an inert diluent from the upper section of the absorption vessel; and
      (ii) a liquid effluent comprising epoxybutene, the absorbent and water from the lower section of the absorption vessel; and
   II. feeding the liquid effluent of step (ii) above to an extraction zone wherein the effluent is intimately contacted with an inert, water-immiscible, liquid extractant to obtain:
      (iii) a first liquid effluent comprising the water-immiscible, liquid extractant and epoxybutene; and
      (iv) a second liquid effluent comprising the absorbent and water from which epoxybutene has been depleted.

2. Process according to claim 1 wherein the water-miscible, liquid absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof.

3. Process according to claim 1 wherein the water-immiscible, liquid extractant is a liquid organic compound from hydrocarbons, halocarbons, esters, ethers, ketones, carbonates or a mixture of any 2 or more thereof.

4. Process according to claim 1 wherein the absorption vessel is operated at a temperature of about to 60° C. and a pressure of about 2.5 to 7.5 bars absolute, the substantially-gaseous effluent is fed to the lower section of the absorption vessel, the absorbent is fed to the upper section of the absorption vessel, and liquid effluent (ii) comprises about 5 to 20 weight percent epoxybutene, the extraction zone and its contents are operated at a temperature of from about 5 to 50° C. and a pressure at or above about 1.0 bars absolute.

5. Process according to claim 1 wherein the absorption vessel is operated at a temperature of about 5 to 60° C. and a pressure of about 2.5 to 7.5 bars absolute, the substantially-gaseous effluent is fed to the lower section of the absorption vessel, the absorbent is fed to the upper section of the absorption vessel, and liquid effluent (ii) comprises about 5 to 20 weight percent epoxybutene, the extraction zone and its contents are operated at a temperature of from about 5 to 50° C. and a pressure at or above about 1.0 bars absolute; the extraction zone is operated at a temperature of about 5 to 50° C.; the liquid effluent (iii) comprises about 5 to 35 weight percent epoxybutene, about 60 to 90 weight percent water-immiscible extractant, 0.5 to 5 weight percent butadiene, and less than about 5 weight percent organic absorbent.

6. Process according to claim 5 wherein the absorbent is selected from 1-methyl-2-pyrrolidinone (NMP), pyridine, 3-butene-1,2-diol (1,2-diol), propylene glycol, dimethylformamide, dimethylacetamide, diethylformamide, diethylacetamide, acetonitrile, dimethylsulphoxide, morpholine, diethylene glycol dimethyl ether, triethylene glycol dimethyl ether, tetraethylene glycol dimethyl ether, propylene glycol monomethyl ether acetate, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether.

7. Process according to claim 5 wherein the water-immiscible extractant is selected from straight- and branched-chain acyclic alkanes containing 4 to 25 carbon atoms; alkenes containing 5 to 25 carbon atoms; cyclic alkanes containing 4 to 5 or 8 to 25 carbon atoms; aromatic hydrocarbons containing 7 to 25 carbon atoms, chloro-, fluoro-, and chlorofluoro-hydrocarbons containing 1 to 25 carbon atoms with boiling points greater than about 0° C.; acyclic ethers containing 6 to 25 carbon atoms; cyclic ethers containing 8 to 25 carbon atoms; acyclic ketones containing 8 to 25 carbon atoms; cyclic ketones containing 10 to 25 carbon atoms; alkyl, alkenyl and aryl esters of alkanoic acids containing a total of about 6 to 25 carbon atoms; alkyl, aryl, and cyclic carbonates containing 4 to 25 carbon atoms.

8. Process according to claim 5 wherein the water-immiscible extractant is selected from n-butane, isobutane, isopentane, n-hexane, cyclohexane, heptane, isooctane, n-octane, nonane, decane, undecane, dodecane, Stoddard solvent, cyclopentane, VMP Naphtha, mixed aliphatic hydrocarbons selected from ExxonMobil solvents Isopar G, H, L, M, and Ashland Solvent 140, 1,3-butadiene, isoprene, vinylcyclohexene, octenes, nonenes and decenes, limonene, benzene, toluene, p-xylene, m-xylene, o-xylene, mesitylene, 1,3-diisopropylbenzene, 1-methylnaphthalene, 1,2,3,4-tetrahydronaphthalene, carbon tetrachloride, chloroform, 1,2-dichlorobenzene, isobutyl isobutyrate, 2,2,4-trimethyl-1,3-pentandiol diisobutyrate, n-butyl propionate, isobutyl propionate, n-propyl butyrate, isopropyl butyrate, isopropyl isobutyrate, n-butyl butyrate, 2-ethylhexyl acetate, methyl benzoate, isopentyl acetate, pentyl acetate, diisobutyl ketone, and mixtures of any two or more thereof.

9. Process according to claim 5 wherein the absorbent is 3-butene-1,2-diol or 1-methyl-2-pyrrolidinone.

10. Process according to claim 5 wherein the water-immiscible extractant is n-decane, n-heptane, isobutyl isobutyrate, p-xylene, 1,2-dichlorobenzene, isopentyl acetate, or butyl propionate.

11. Process according to claim 1 wherein gaseous effluent (1) is fed to a water wash column to produce a liquid effluent comprising water and absorbed water-miscible absorbent and a gaseous effluent comprising butadiene, oxygen, inert diluent and less 50 ppmv water-miscible absorbent and the gaseous effluent is recycled to an epoxidation zone wherein butadiene is oxidized to epoxybutene.

12. Process for the recovery and purification of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises the steps of:

I. feeding the effluent to an absorption vessel wherein the effluent is intimately contacted with a water-miscible, liquid absorbent to obtain:
  (i) a gaseous effluent comprising butadiene, oxygen and an inert diluent from the upper section of the absorption vessel; and
  (ii) a liquid effluent comprising epoxybutene, the absorbent and water from the lower section of the absorption vessel; and II. feeding the liquid effluent of step (ii) above to an extraction zone wherein the effluent is intimately contacted with an inert, water-immiscible, liquid extractant to obtain:
  (iii) a first liquid effluent comprising the water-immiscible, liquid extractant and epoxybutene; and
  (iv) a second liquid effluent comprising the absorbent and water from which epoxybutene has been depleted;

III. feeding liquid effluent (iii) of step II. to the middle section of a first distillation column to obtain (1) a distillate effluent comprising epoxybutene and water from the upper section of the distillation vessel and (2) a liquid effluent comprising the extractant from the lower section of the distillation vessel;

IV. allowing distillate (1) from step III. to form two phases comprising an epoxybutene-rich phase and a water-rich phase; and V. feeding the epoxybutene-rich phase from step IV to the upper section of an epoxybutene purification distillation column to obtain (1) a distillate effluent comprising epoxybutene and water from the upper section of the distillation vessel; and (2) an effluent comprising (a) liquid epoxybutene from the lower section of the distillation column or (b) liquid or gaseous epoxybutene from the side of the distillation column.

13. Process according to claim 12 wherein the water-miscible, liquid absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof.

14. Process according to claim 12 wherein the water-immiscible, liquid extractant is a liquid organic compound from hydrocarbons, halocarbons, esters, ethers, ketones, carbonates or a mixture of any 2 or more thereof.

15. Process according to claim 12 wherein the absorption vessel is operated at a temperature of about 5 to 60° C. and a pressure of about 2.5 to 7.5 bars absolute, the substantially-gaseous effluent is fed to the lower section of the absorption vessel, the absorbent is fed to the upper section of the absorption vessel, and liquid effluent (ii) comprises about 5 to 20 weight percent epoxybutene, the extraction zone and its contents are operated at a temperature of from about 5 to 50° C. and a pressure at or above about 1.0 bars absolute.

16. Process according to claim 12 wherein the absorption vessel is operated at a temperature of about 5 to 60° C. and a pressure of about 2.5 to 7.5 bars absolute, the substantially-gaseous effluent is fed to the lower section of the absorption vessel, the absorbent is fed to the upper section of the absorption vessel, and liquid effluent (ii) comprises about 5 to 20 weight percent epoxybutene, the extraction zone and its contents are operated at a temperature of from about 5 to 50° C. and a pressure at or above about 1.0 bars absolute; the extraction zone is operated at a temperature of about 5 to 50° C.; the liquid effluent (iii) comprises about 5 to 35 weight percent epoxybutene, about 60 to 90 weight percent water-immiscible extractant, 0.5 to 5 weight percent butadiene, and less than about 5 weight percent organic absorbent.

17. Process according to claim 16 wherein the absorbent is selected from 1-methyl-2-pyrrolidinone (NMP), pyridine, 3-butene-1,2-diol (1,2-diol), propylene glycol, dimethylformamide, dimethylacetamide, diethylformamide, diethylacetamide, acetonitrile, dimethylsulphoxide, morpholine, diethylene glycol dimethyl ether, triethylene glycol dimethyl ether, tetraethylene glycol dimethyl ether, propylene glycol monomethyl ether acetate, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether.

18. Process according to claim 16 wherein the water-immiscible extractant is selected from straight- and branched-chain acyclic alkanes containing 4 to 25 carbon atoms; alkenes containing 5 to 25 carbon atoms; cyclic alkanes containing 4 to 5 or 8 to 25 carbon atoms; aromatic hydrocarbons containing 7 to 25 carbon atoms, chloro-, fluoro-, and chlorofluoro-hydrocarbons containing 1 to 25 carbon atoms with boiling points greater than about 0° C.; acyclic ethers containing 6 to 25 carbon atoms; cyclic ethers containing 8 to 25 carbon atoms; acyclic ketones containing 8 to 25 carbon atoms; cyclic ketones containing 10 to 25 carbon atoms; alkyl, alkenyl and aryl esters of alkanoic acids containing a total of about 6 to 25 carbon atoms; alkyl, aryl, and cyclic carbonates containing 4 to 25 carbon atoms.

19. Process according to claim 16 wherein the water-immiscible extractant is selected from n-butane, isobutane, isopentane, n-hexane, cyclohexane, heptane, isooctane, n-octane, nonane, decane, undecane, dodecane, Stoddard solvent, cyclopentane, VMP Naphtha, mixed aliphatic hydrocarbons selected from ExxonMobil solvents Isopar G, H, L, M, and Ashland Solvent 140, 1,3-butadiene, isoprene, vinylcyclohexene, octenes, nonenes and decenes, limonene, benzene, toluene, p-xylene, m-xylene, o-xylene, mesitylene, 1,3-diisopropylbenzene, 1-methylnaphthalene, 1,2,3,4-tetrahydronaphthalene, carbon tetrachloride, chloroform, 1,2-dichlorobenzene, isobutylisobutyrate, 2,2,4-trimethyl-1,3-pentandiol diisobutyrate, n-butyl propionate, isobutyl propionate, n-propyl butyrate, isopropylbutyrate, isopropylisobutyrate, n-butylbutyrate, 2-ethylhexyl acetate, methyl benzoate, isopentyl acetate, pentyl acetate, diisobutyl ketone, and mixtures of any two or more thereof.

20. Process according to claim 16 wherein the absorbent is 3-butene-1,2-diol or 1-methyl-2-pyrrolidinone.

21. Process according to claim 16 wherein the water-immiscible extractant is n-decane, n-heptane, isobutyl isobutyrate, p-xylene, 1,2-dichlorobenzene, isopentyl acetate, or butyl propionate.

22. Process according to claim 12 wherein gaseous effluent (1) is fed to a water wash column to produce a liquid effluent comprising water and absorbed water-miscible absorbent and a gaseous effluent comprising butadiene, oxygen, inert diluent and less 50 ppmv water-miscible absorbent and the gaseous effluent is recycled to an epoxidation zone wherein butadiene is oxidized to epoxybutene.

23. Process according to claim 12 the first distillation column (extractant recovery column) of step III is operated at a top temperature of about 60 to 105° C. and a base temperature of about 100 to 220° C. and a pressure of about 0.1 to 4 bars absolute and the epoxybutene purification distillation column is operated at a top temperature of about 60 to 75° C. and a base temperature of about 67 to 120° C. and a pressure of about 1 to 4 bars absolute.

24. Process according to claim 7 wherein the water-rich phase of step IV is fed to the upper section of a third distillation column (water column) to obtain a vaporous distillate product comprising epoxybutene and water from the top of the column and a liquid product comprising water from the base of the reactor.

25. Process according to claim 24 wherein vaporous distillate product comprises about 15 to 50 weight percent water and 50 to 85 weight percent epoxybutene and liquid product consists essentially of water and trace amounts of epoxybutene and epoxybutene-water reaction products.

26. Process according to claim 16 wherein epoxybutene product (2) from step V. has a purity of greater than 99.5 weight percent epoxybutene.

* * * * *